US008404818B2

(12) United States Patent
Chen et al.

(10) Patent No.: US 8,404,818 B2
(45) Date of Patent: Mar. 26, 2013

(54) MONOCLONAL ANTIBODIES AGAINST ORTHOPOXVIRUSES

(75) Inventors: **

Related U.S. Application Data

(60) Provisional application No. 60/779,855, filed on Mar. 7, 2006, provisional application No. 60/753,437, filed on Dec. 22, 2005.

(56) References Cited

OTHER PUBLICATIONS

Moss, "Poxvirus entry and membrane fusion," *Virology*, vol. 344, pp. 48-54, 2005.

Payne, "Significance of Extracellular Enveloped Virus in the in vitro and in vivo Dissemination of Vaccinia," *J Gen Virol*, vol. 50, pp. 89-100, 1980.

Sanderson et al., "Roles of vaccinia virus EEV-specific proteins in intracellular actin tail formation and low pH-induced cell-cell fusion" *J Gen Virol*, vol. 79, pp. 1415-1425, 1998.

Schmelz et al., "Assembly of Vaccinia Virus: the Second Wrapping Cisterna is Derived from the Trans Golgi Network," *J Virol*, vol. 68, pp. 130-147, 1994.

Schofield et al, "Four Chimpanzee Monoclonal Antibodies Isolated by Phage Display Neutralize Hepatitis A Virus," *Virology*, vol. 292, pp. 127-136, 2002.

Smith et al, "Extracellular enveloped vaccinia virus, Entry, egress, and evasion,"*Adv Exp Med Biol*, vol. 440, pp. 395-414, 1998.

Vanderplasschen et al., "Intracellular and Extracellular vaccinia virions enter cells by different mechanisms," *J Gen Virol*, vol. 79, pp. 877-887, 1998.

Wolffe et al., "Deletion of the Vaccinia Virus B5R Gene Encoding a 42-Kilodalton Membrane Glycoprotein Inhibits Extracellular Virus Envelope Formation and Dissemination," *J Virol*, vol. 67, pp. 4732-4741, 1993.

Carayannopolous et al. in Fundamental Immunology, edited by William E. Paull, 3$^{rd}$ Edition, 1993, pp. 283-314.

Rudikoff et al. Proc Natl. Acad. Sci. USA 1982 vol. 79: p. 1979.

\* cited by examiner a. VH (8AH)

```
        FWR1                        CDR1        FWR2
EVQLLESGGGLIKPGGSLRLSCAASGFIFR     DYNIN       WVRQAPGKGLEWLG
    CDR2                       FWR3
FIRTRASGRSTE          YSASVKGRFTISRDDSKNIAYLHINSLKMEDTAVYYCAK
    CDR3              FWR4
KGDSYYYMDF            WGKGTAVTVS
``` b. VL

```
            FWR1                        CDR1              FWR2
8AL   ELALTQPASVSGSPGQSITISC       TGGRSDLGDSNFVS      WYQQYPGKAPKLLIY
7AL   -------P--------------       --TS--V-GH-G--      -----------VM--

CDR2              FWR3                              CDR3
8AL   QVNKRPS    GVPDRFSASKSANTASLTISGLQTEDEADYFC      SSYTTTSTYV
7AL   E------    --SN-L-G---G-----------A---G--Y-      ---RNGGSV-

FWR4
8AL   FGIGTKVVVLGQ
7AL   --G---LT----
``` c.

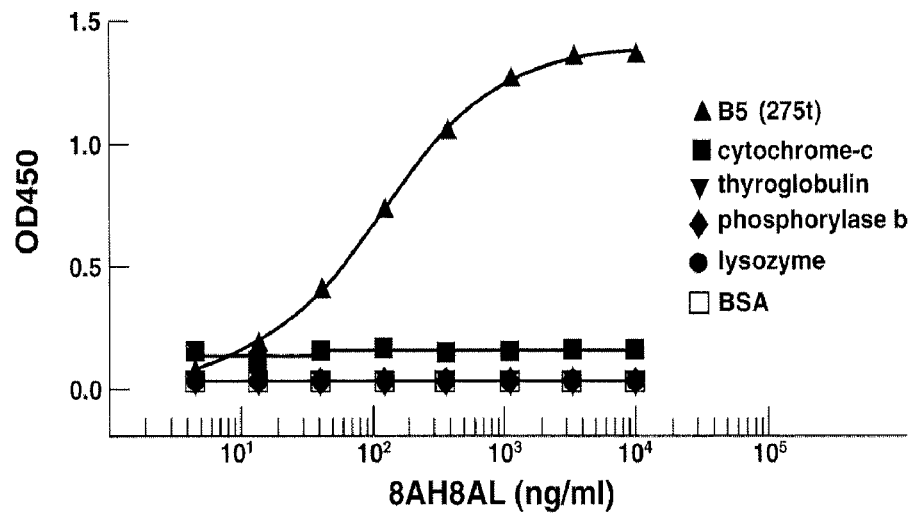

*Figure 1* a. VH

```
              FRW1                        CDR1   FRW2              CDR2
6CH    EVQLEQSGSEVKKPGASVKLSCKASGYTFT SYSLG WVRQAPGQGLEWMG WINTKTGNPT
12CH   ----S--A--------------V------- K-TIH ------R------ ----AV--TK
12FH   ----S--A------E-L-I----G----A --WIV ----M-K----Y-- S-YPGDSGTR

FRW3                                   CDR3
6CH    YAQGFTGRFVFSLDTSVNTAYLQITSLKAEDTAVYFCAK G*TFYYGWGPY**YNWFDP
12CH   FS-SLQ--VTITR----A-----MELS--RS-----I-Y--R DPIL-----S-RVAGY--Y
12FH   -SPS-R-QVTI-A-K-I------WG------S---F-Y--R LKPLRGSLFGEP*IGPY-Y

FRW4
6CH    WGQGALVTV
12CH   -----S---
12FH   ---AT----
``` b. VL

```
              FRW1                       CDR1        FRW2              CDR2
6CL    AELVLTQPPSVSVSAAPGQKITISC SGSGSNIG*RHYVS WYQQFPGTAPKILIY DNDKRPS
12FL   ---A-----A---GS---S------ T-TS-DV-GYNA-- ----H--K---LM-- EVN----
12CL   ---------VY---TAS-T- --DKLGDK****------- ----KSAQP-VLV-H GDN----

FRW3                       CDR3              FRW4
6CL    GISDRFSGSKSGASATLDITGLQTGDEADYYC ATWDTNLSGGV FGGGTKVTVLGQ
12FL   -V-N--------NT-S-T-S---AE------- SSYRS*GGTV- -------L----
12CL   --PE-----N--NT----T-S-T-AI------ Q---S*YTFLL ------L-A-S-
```

*Figure 6*

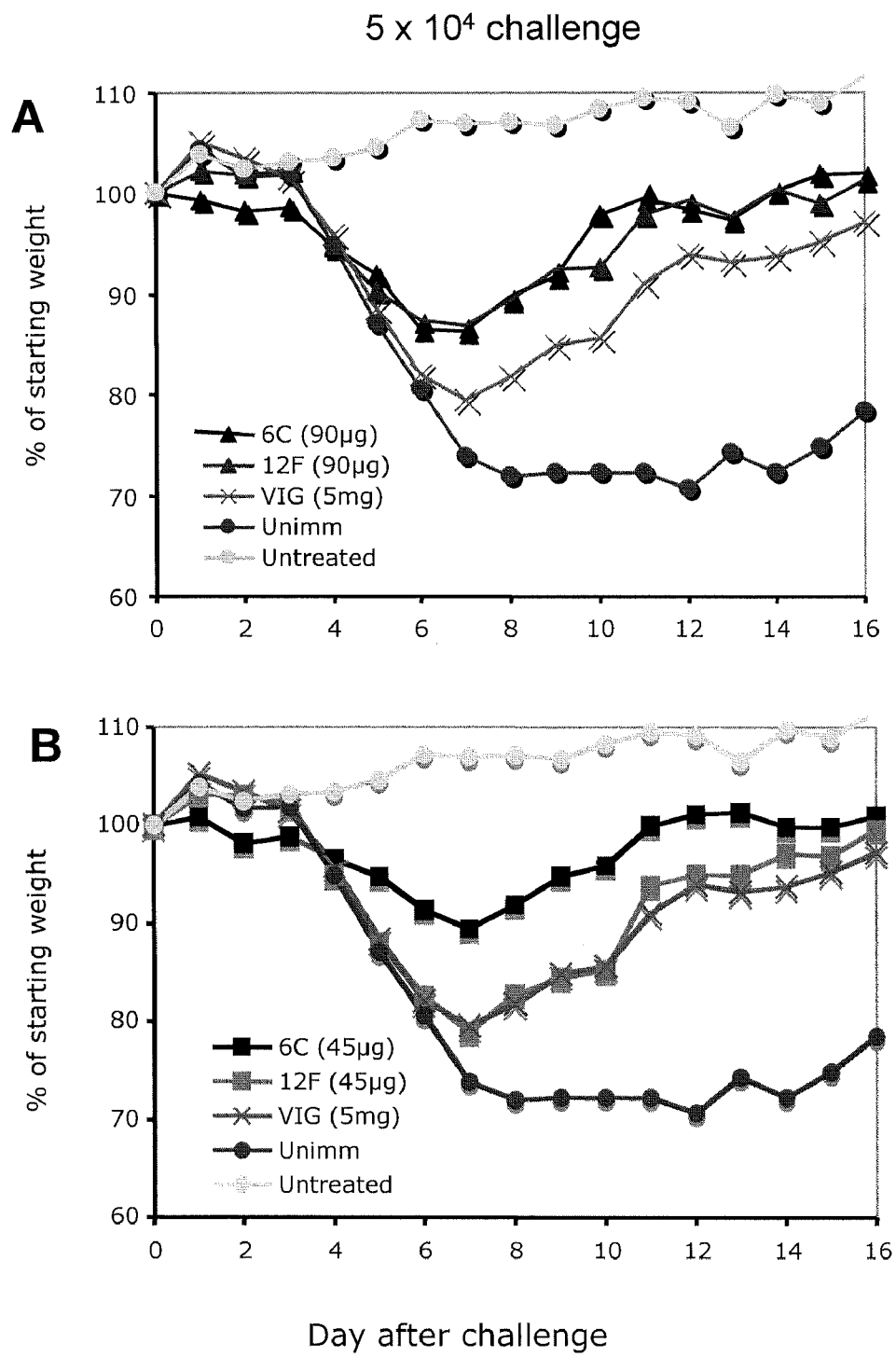
Figure 15 A, B

MONOCLONAL ANTIBODIES AGAINST ORTHOPOXVIRUSES

CROSS REFERENCE TO RELATED APPLICATIONS

This application is a divisional of U.S. patent application Ser. No. 12/142,594, Filed Jun. 19, 2008; which is a continuation of and claims the benefit of priority to International Application No. PCT/US2006/048832 filed Dec. 22, 2006, which designated the United States and was published in English, and U.S. patent application Ser. No. 12/142,594 is a continuation of and claims the benefit of priority to International Application No. PCT/US2006/048833 filed Dec. 22, 2006, which designated the United States and was published in English; wherein both of the aforementioned international applications claim the benefit of priority to U.S. Provisional Application No. 60/779,855, filed Mar. 7, 2006, U.S. Provisional Application No. 60/763,786, filed Jan. 30, 2006, and U.S. Provisional Application No. 60/753,437, filed Dec. 22, 2005. All of the aforementioned applications are hereby expressly incorporated by reference in their entireties.

SEQUENCE LISTING

The present application is being filed along with a Sequence Listing in electronic format. The Sequence Listing is provided as a file entitled NIH307_001C1_Sequence_Listing.TXT, created Jun. 19, 2008, which is 27 Kb in size. The information in the electronic format of the Sequence Listing is incorporated herein by reference in its entirety.

FIELD OF THE INVENTION

This invention relates generally to the field of immunology and specifically to monoclonal antibodies that bind or neutralize Orthopoxviruses.

BACKGROUND OF THE INVENTION

Concerns that variola (smallpox) virus might be used as a biological weapon have led to the recommendation of widespread vaccination with vaccinia virus (VACV) (Henderson, D. A. 1999 *Science* 283:1279-1282). While vaccination is generally safe and effective for prevention of smallpox, it is well documented that various adverse reactions in individuals have been caused by vaccination with existing licensed vaccines (Fulginiti, V. A. et al. 2003 *Clin Infect Dis* 37:251-271). Vaccinia immune globulin (VIG) prepared from vaccinated humans has historically been used to treat adverse reactions arising from VACV immunization (Kempe, C. H. 1960 *Pediatrics* 26:176-189; Feery, B. J. (1976) *Vox Sang* 31:68-76; Hopkins, R. J. et al. 2004 *Clin Infect Dis* 39:759-766; Hopkins, R. J. & Lane, J. M. 2004 *Clin Infect Dis* 39:819-826) and to date, VIG is still the only recommended treatment (Hopkins, R. J. et al. 2004 *Clin Infect Dis* 39:759-766; Hopkins, R. J. & Lane, J. M. 2004 *Clin Infect Dis* 39:819-826). However, VIG lots may have different potencies and carry the potential to transmit other viral agents.

VACV is the prototype virus in the genus Orthopoxvirus, which includes variola virus, the causative agent of smallpox. There are two major forms of infectious VACV: intracellular mature virus (MV) and extracellular enveloped virus (EV). The majority of the MV remains within the cell until lysis, but some are wrapped in additional membranes and exocytosed as EV. Most EV remains attached to the outside of the plasma membrane and is responsible for direct cell-to-cell spread; however some are released into the medium and can cause comet-like satellite plaques (Blasco, R. & Moss, B. 1992 *J Virol* 66:4170-4179; Blasco, R. et al. 1993 *J Virol* 67:3319-3325). The EV is important for virus dissemination in vivo as well as in cultured cells (Payne, L. G. 1980 *J Gen Virol* 50:89-100; Smith, G. L. & Vanderplasschen, A. 1998 *Adv Exp Med Biol* 440:395-414). Because an EV is essentially an MV enclosed by an additional membrane, the two forms of VACV have different outer proteins and bind to cells differently (Vanderplasschen, A. et al. 1998 *J Gen Virol* 79:877-887), though ultimately only the proteins of the MV membrane mediate membrane fusion (Moss, B. 2005 *Virology* 344:48-54). B5 is one of five known EV-specific proteins and is highly conserved among different strains of VACV as well as in other orthopoxviruses (Engelstad, M. et al 1992 *Virology* 188:801-810; Isaacs, S. N. et al. 1992 *J Virol* 66:7217-7224). B5 is a 42-kDa glycosylated type I membrane protein with a large ectodomain composed of four small domains that are similar to short consensus repeat (SCR) domains of complement regulatory protein (Engelstad, M. et al 1992 *Virology* 188:801-810; Isaacs, S. N. et al. 1992 *J Virol* 66:7217-7224) although no complement regulatory activity has been demonstrated. B5 is required for efficient envelopment of MV, as well as for actin tail formation, normal plaque size and virulence (Engelstad, M. & Smith, G. L. 1993 *Virology* 194:627-637; Sanderson, C. M. et al. 1998 *J Gen Virol* 79:1415-1425; Wolffe, E. J. et al. 1993 *J Virol* 67:4732-4741).

The B5 protein is an important target for neutralizing antibodies: antisera to B5 can neutralize EV in a plaque reduction assay and inhibit "comet formation", the in vitro manifestation of cell-to-cell spread of EV (Engelstad, M. et al 1992 *Virology* 188:801-810, Galmiche, M. C. et al. 1999 *Virology* 254:71-80; Law, M. & Smith, G. L. 2001 *Virology* 280:132-142; Aldaz-Carroll et al. 2005 *J Virol* 79:6260-6271). Recent studies showed that anti-B5 in VIG was responsible for most of the neutralizing activity against EV as measured by a plaque reduction assay (Bell, E. et al. 2004 *Virology* 325:425-431). To date, rat and mouse anti-B5 neutralizing MAbs have been reported (Aldaz-Carroll et al. 2005 *J Virol* 79:6260-6271; Schmelz, M. et al. 1994 *J Virol* 68:130-147) and the epitopes recognized by mouse MAbs have been mapped to the border of SCR1-SCR2 and/or the stalk of B5 (Aldaz-Carroll et al. 2005 *J Virol* 79:6260-6271). In addition, a rat monoclonal antibody (MAb) to B5 provided protection in a VACV mouse challenge model (Lustig, S. et al. 2005 *J Virol* 79:13454-13462).

SEGUE TO THE INVENTION

We decided to obtain therapeutically useful high-affinity monoclonal antibodies to B5 protein from chimpanzees because of the extreme similarity of their IgG with human IgG (Ehrlich, P. H. et al. 1990 *Hum Antibodies Hybridomas* 1:23-26; Schofield, D. J. et al. 2002 *Virology* 292:127-136). A phage display library bearing Fabs was derived from the bone marrow of chimpanzees that had been vaccinated with VACV. From this library, we isolated and characterized two potent anti-B5 antibodies that neutralize variola virus in addition to VACV. Such human-like monoclonal antibodies against B5 are contemplated as providing superior protection with a lower dose and higher safety profile than VIG.

SUMMARY OF THE INVENTION

The present invention relates to monoclonal antibodies that bind or neutralize Orthopoxviruses. The invention provides such antibodies, fragments of such antibodies retaining B5 or A33 binding ability, fully human antibodies retaining B5 or A33 binding ability, and pharmaceutical compositions including such antibodies. The invention further provides for isolated nucleic acids encoding the antibodies of the invention and host cells transformed therewith. Additionally, the invention provides for prophylactic, therapeutic, and diagnostic methods employing the antibodies and nucleic acids of the invention.

BRIEF DESCRIPTION OF THE DRAWINGS

FIG. 1. Amino acid sequences of variable domains of heavy (a) (8AH8AL—SEQ ID NO: 1 and 8AH7AL—SEQ ID NO: 17) and light (b) (8AH8AL—SEQ ID NO: 9 and 8AH7AL—SEQ ID NO: 25) chains of chimpanzee/human anti-B5 MAbs and ELISA titration of anti-B5 8AH8AL. Complementarity-determining regions (CDR1, CDR2, and CDR3) and framework regions (FWR1, FWR2, FWR3, and FWR4) are indicated above the sequence or sequence alignment. Dashes indicate an identical residue. (c), For the ELISA binding assay, the wells of ELISA plates were coated with recombinant B5 (275t) or unrelated proteins (BSA, thyroglobulin, lysozyme, and phosphorylase-b) and then incubated with 8AH8AL at various concentrations. Bound IgG was detected by the addition of peroxidase-conjugated anti-human (Fab)$_2$ followed by TMB substrate.

FIG. 6. Sequences of (a) VH (6C—SEQ ID NO: 33; 12C—SEQ ID NO: 49; and 12F—SEQ ID NO: 65) and (b) (6C—SEQ ID NO: 41; 12C—SEQ ID NO: 57; and 12F—SEQ ID NO: 73) VL of MAbs against A33 proteins of vaccinia virus.

TABLE A

Figure 2:
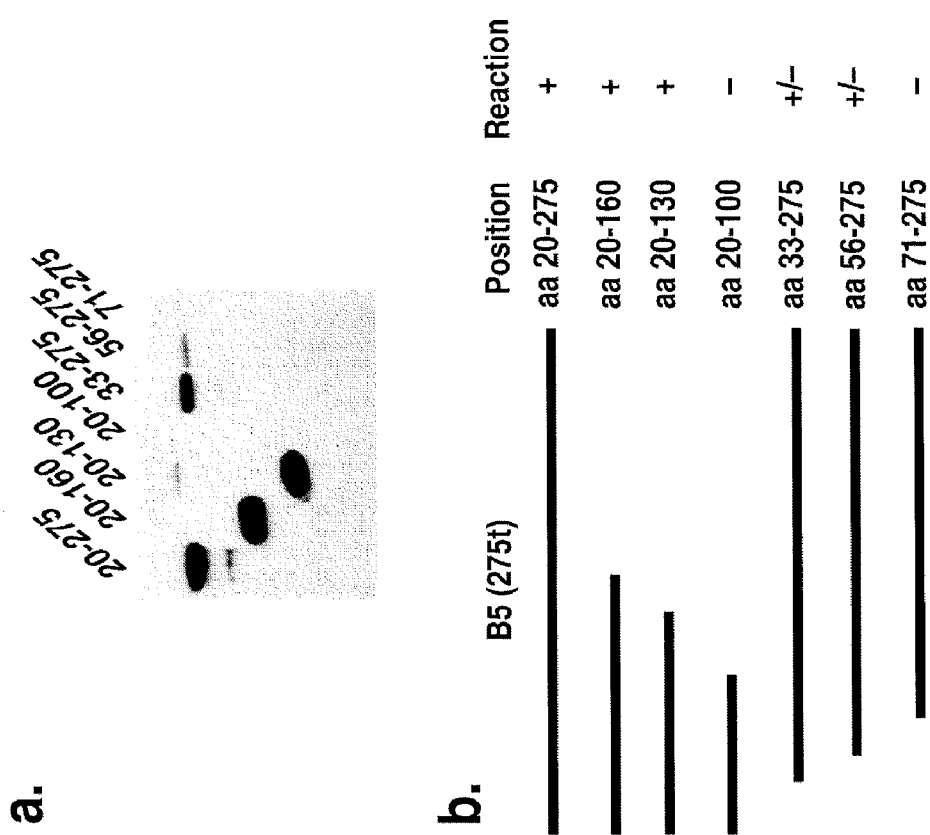
FIG. 2. Epitope mapping by Western blotting. Similar amounts of different-sized fragments of B5 expressed in bacteria were blotted onto the membrane and anti-B5 MAb was added (a). The bound anti-B5 was detected by HRP-conjugated anti-human IgG (Fab')$_2$. The positive bands were visualized with addition of LumiGLO chemiluminescent peroxidase substrate and exposing the membrane to X-ray film. The result was summarized in (b), where the peptides that reacted with antibody were scored as positive (+). Faint intensity of the bands was scored as +/−. The numbers denote the starting and ending amino acid.

Brief Description of Mab SEQ ID NOs

| | Heavy Chain SEQ ID NOs | | | | | | | | Light Chain SEQ ID NOs | | | | | | | |
|---|---|---|---|---|---|---|---|---|---|---|---|---|---|---|---|---|
| Fab/mab | $V_H$ | FR1 | CDR1 | FR2 | CDR2 | FR3 | CDR3 | FR4 | $V_L$ | FR1 | CDR1 | FR2 | CDR2 | FR3 | CDR3 | FR4 |
| Anti-B5 8AH8AL | 1 | 2 | 3 | 4 | 5 | 6 | 7 | 8 | 9 | 10 | 11 | 12 | 13 | 14 | 15 | 16 |
| Anti-B5 8AH7AL | 17 | 18 | 19 | 20 | 21 | 22 | 23 | 24 | 25 | 26 | 27 | 28 | 29 | 30 | 31 | 32 |
| Anti-A33 6C | 33 | 34 | 35 | 36 | 37 | 38 | 39 | 40 | 41 | 42 | 43 | 44 | 45 | 46 | 47 | 48 |
| Anti-A33 12C | 49 | 50 | 51 | 52 | 53 | 54 | 55 | 56 | 57 | 58 | 59 | 60 | 61 | 62 | 63 | 64 |
| Anti-A33 12F | 65 | 66 | 67 | 68 | 69 | 70 | 71 | 72 | 73 | 74 | 75 | 76 | 77 | 78 | 79 | 80 |

DEPOSIT OF BIOLOGICAL MATERIAL

The following biological material has been deposited in accordance with the terms of the Budapest Treaty with the American Type Culture Collection (ATCC), Manassas, Va., on the date indicated:

| Biological material | Designation No. | Date |
|---|---|---|
| Chimpanzee anti-vaccinia virus B5 protein Fab in pComb 3H vector, 8AH8AL | PTA-7294 | Dec. 22, 2005 |

Chimpanzee anti-vaccinia virus B5 protein Fab in pComb 3H vector, 8AH8AL, was deposited as ATCC Accession No. PTA-7294 on Dec. 22, 2005 with the American Type Culture Collection (ATCC), 10801 University Blvd., Manassas, Va. 20110-2209, USA. This deposit was made under the provisions of the Budapest Treaty on the International Recognition of the Deposit of Microorganisms for the Purposes of Patent Procedure and the Regulations there under (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14). Availability of the deposited biological material is not to be construed as a license to practice the invention in contravention of the rights granted under the authority of any government in accordance with its patent laws.

| Biological material | Designation No. | Date |
|---|---|---|
| Chimpanzee anti-vaccinia virus A33 protein Fab in pComb 3H vector, 6C | PTA-7323 | Jan. 18, 2006 |

Chimpanzee anti-vaccinia virus A33 protein Fab in pComb 3H vector, 6C, was deposited as ATCC Accession No. PTA-7323 on Jan. 18, 2006 with the American Type Culture Collection (ATCC), 10801 University Blvd., Manassas, Va. 20110-2209, USA. This deposit was made under the provisions of the Budapest Treaty on the International Recognition of the Deposit of Microorganisms for the Purposes of Patent Procedure and the Regulations there under (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14). Availability of the deposited biological material is not to be construed as a license to practice the invention in contravention of the rights granted under the authority of any government in accordance with its patent laws.

| Biological material | Designation No. | Date |
|---|---|---|
| Chimpanzee anti-vaccinia virus A33 protein Fab in pComb 3H vector, 12F | PTA-7324 | Jan. 18, 2006 |

Chimpanzee anti-vaccinia virus A33 protein Fab in pComb 3H vector, 12F, was deposited as ATCC Accession No. PTA-7324 on Jan. 18, 2006 with the American Type Culture Collection (ATCC), 10801 University Blvd., Manassas, Va. 20110-2209, USA. This deposit was made under the provisions of the Budapest Treaty on the International Recognition of the Deposit of Microorganisms for the Purposes of Patent Procedure and the Regulations there under (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14). Availability of the deposited biological material is not to be construed as a license to practice the invention in contravention of the rights granted under the authority of any government in accordance with its patent laws.

DETAILED DESCRIPTION OF THE PREFERRED EMBODIMENT

Vaccinia Virus Strain WR

The complete genome sequence of the vaccinia virus strain WR, including B5R (B5) and A33R (A33), can be obtained at Genbank Accession No. AY243312.

Definitions

Unless defined otherwise, technical and scientific terms used herein have the same meaning as commonly understood by one of ordinary skill in the art to which this invention belongs. See, e.g., Singleton P and Sainsbury D., *Dictionary of Microbiology and Molecular Biology* $3^{rd}$ ed., J. Wiley & Sons, Chichester, New York, 2001, and *Fields Virology* $4^{th}$ ed., Knipe D. M. and Howley P. M. eds, Lippincott Williams & Wilkins, Philadelphia 2001.

As used herein, the term "antibody" means an immunoglobulin molecule or a fragment of an immunoglobulin molecule having the ability to specifically bind to a particular antigen. Antibodies are well known to those of ordinary skill in the science of immunology. As used herein, the term "antibody" means not only full-length antibody molecules but also fragments of antibody molecules retaining antigen binding ability. Such fragments are also well known in the art and are regularly employed both in vitro and in vivo. In particular, as used herein, the term "antibody" means not only full-length immunoglobulin molecules but also antigen binding active fragments such as the well-known active fragments $F(ab')_2$, Fab, Fv, and Fd.

As used herein, the term "Orthopoxvirus infection" means an infection by an Orthopoxvirus. Four Orthopoxvirus species; three of which are zoonotic, may infect humans: (a) variola virus, the cause of smallpox, which is eradicated, is a strictly human pathogen producing a febrile pustular rash illness; (b) monkeypox virus, which is reported from nine West and Central African rainforest countries, mainly the Democratic Republic of Congo (DRC, formerly Zaire), is a zoonotic agent of a smallpox-like illness of low interhuman transmissibility; (c) cowpox virus is rodent-borne and indigenous to rodents in several European and a few western Asian countries, where humans appear to acquire a localized pustular skin infection by contact with infected rodents, or more likely, intermediate hosts, such as pet cats, cows, or other animals; and (d) the vaccinia virus subspecies buffalopox virus, which occurs mainly on the Indian subcontinent, causes localized oral and skin lesions after contact with infected dairy animals or drinking their milk. In addition, vaccinia virus strains used for smallpox vaccination form a dermal pustule and may cause postvaccinal side effects.

As used herein with respect to polypeptides, the term "substantially pure" means that the polypeptides are essentially free of other substances with which they may be found in nature or in vivo systems to an extent practical and appropriate for their intended use. In particular, the polypeptides are sufficiently pure and are sufficiently free from other biological constituents of their host's cells so as to be useful in, for example, generating antibodies, sequencing, or producing pharmaceutical preparations. By techniques well known in the art, substantially pure polypeptides may be produced in light of the nucleic acid and amino acid sequences disclosed herein. Because a substantially purified polypeptide of the invention may be admixed with a pharmaceutically acceptable carrier in a pharmaceutical preparation, the polypeptide may comprise only a certain percentage by weight of the preparation. The polypeptide is nonetheless substantially pure in that it has been substantially separated from the substances with which it may be associated in living systems.

As used herein with respect to nucleic acids, the term "isolated" means: (1) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences, as desired.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

Novel Anti-B5 and Anti-A33 Monoclonal Antibodies

The present invention derives, in part, from the isolation and characterization of novel chimpanzee Fab fragments and their humanized monoclonal antibodies that selectively bind Orthopoxvirus B5 or A33 antigens. Additionally, these new monoclonal antibodies have been shown to neutralize Orthopoxviruses. The paratopes of the anti-B5 and anti-A33 Fab fragments associated with the neutralization epitope on the B5 and A33 antigens are defined by the amino acid (aa) sequences of the immunoglobulin heavy and light chain V-regions described in FIGS. 1 and 6 and in SEQ ID NO: 1 through SEQ ID NO: 80 of Table A. The nucleic acid sequences coding for these amino acid sequences were identified by sequencing the Fab heavy chain and light chain fragments. Due to the degeneracy of the DNA code, the paratope is more properly defined by the derived amino acid sequences depicted in FIGS. 1 and 6 and in SEQ ID NO: 1 through SEQ ID NO: 80 of Table A.

In one set of embodiments, the present invention provides the full-length, humanized anti-B5 or anti-A33 monoclonal antibodies in isolated form and in pharmaceutical preparations. Similarly, as described herein, the present invention provides isolated nucleic acids, host cells transformed with nucleic acids, and pharmaceutical preparations including isolated nucleic acids, encoding the full-length, humanized monoclonal antibody of the anti-B5 or anti-A33 monoclonal antibodies. Finally, the present invention provides methods, as described more fully herein, employing these antibodies and nucleic acids in the in vitro and in vivo diagnosis, prevention and therapy of Orthopoxvirus infection.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of a full-length antibody. Similarly, an antibody from which the Fc region has been enzymatically cleaved, or which has been produced without the Fc region, designated an Fab fragment, retains one of the antigen binding sites of a full-length antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986, supra; Roitt, 1991, supra). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

The complete amino acid sequences of the antigen-binding Fab portion of the anti-B5 or anti-A33 monoclonal antibodies as well as the relevant FR and CDR regions are disclosed herein. SEQ. ID. NOs: 1, 17, 33, 49, and 65 disclose the amino acid sequence of the Fd fragment of anti-B5 or anti-A33 monoclonal antibodies. The amino acid sequences of the heavy chain FR1, CDR1, FR2, CDR2, FR3, CDR3 and FR4 regions are disclosed as (FR1, SEQ. ID. NO: 2, 18, 34, 50, and 66); (CDR1, SEQ ID NOs: 3, 19, 35, 51, and 67); (FR2, SEQ ID NOs: 4, 20, 36, 52 and 68); (CDR2, SEQ ID NOs: 5, 21, 37, 53 and 69); (FR3, SEQ ID NOs: 6, 22, 38, 54 and 70); (CDR3, SEQ ID NOs: 7, 23, 39, 55 and 71); and (FR4, SEQ ID NOs: 8, 24, 40, 56 and 72). SEQ ID NOs: 9, 25, 41, 57 and 73 disclose the amino acid sequences of the light chains of the anti-B5 or anti-A33 monoclonal antibodies. The amino acid sequences of the light chain FR1, CDR1, FR2, CDR2, FR3, CDR3 and FR4 regions are disclosed as (FR1, SEQ ID NOs: 10, 26, 42, 58 and 74); (CDR1, SEQ ID NOs: 11, 27, 43, 59 and 75); (FR2, SEQ ID NOs: 12, 28, 44, 60 and 76); (CDR2, SEQ ID NOs: 13, 29, 45, 61 and 77); (FR3, SEQ ID NOs: 14, 30, 46, 62 and 78); (CDR3, SEQ ID NOs: 15, 31, 47, 63 and 79); (FR4, SEQ ID NOs: 16, 32, 48, 64 and 80).

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of full-length antibodies with antigen-binding ability, are often referred to as "chimeric" antibodies.

Thus, as will be apparent to one of ordinary skill in the art, the present invention also provides for F(ab')$_2$, Fab, Fv and Fd fragments of the 8AH8AL, 8AH7AL, 6C, 12C, or 12F antibody, or other anti-B5 or anti-A33 antibody; chimeric antibodies in which the Fc and/or FR and/or CDR1 and/or CDR2 and/or light chain CDR3 regions of the 8AH8AL, 8AH7AL, 6C, 12C, or 12F antibody, or other anti-B5 or anti-A33 antibody have been replaced by homologous human or non-human sequences; chimeric F(ab')$_2$ fragment antibodies in which the FR and/or CDR1 and/or CDR2 and/or light chain CDR3 regions of the 8AH8AL, 8AH7AL, 6C, 12C, or 12F antibody, or other anti-B5 or anti-A33 antibody have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. Thus, those skilled in the art may alter the 8AH8AL, 8AH7AL, 6C, 12C, or 12F antibody, or other anti-B5 or anti-A33 antibody by the construction of CDR grafted or chimeric antibodies or antibody fragments containing all, or part thereof, of the disclosed heavy and light chain V-region CDR amino acid sequences (Jones, P. T. et al. 1986 *Nature* 321:522-525; Verhoeyen, M. et al. 1988 *Science* 39:1534-1536; and Tempest, P. R. et al. 1991 *Bio/Technology* 9:266-271), without destroying the specificity of the antibodies for the B5 or A33 epitopes. Such CDR grafted or chimeric antibodies or antibody fragments can be effective in prevention and treatment of Orthopoxvirus infection in animals (e.g. cattle) and man.

In preferred embodiments, the chimeric antibodies of the invention are fully human or humanized chimpanzee monoclonal antibodies including at least the heavy chain CDR3 region of the 8AH8AL, 8AH7AL, 6C, 12C, or 12F antibody, or other anti-B5 or anti-A33 antibody. As noted above, such chimeric antibodies may be produced in which some or all of the FR regions of the 8AH8AL, 8AH7AL, 6C, 12C, or 12F antibody, or other anti-B5 or anti-A33 antibody have been replaced by other homologous human FR regions. In addition, the Fc portions may be replaced so as to produce IgA or IgM as well as IgG antibodies bearing some or all of the CDRs of the the 8AH8AL, 8AH7AL, 6C, 12C, or 12F antibody, or other anti-B5 or anti-A33 antibody. Of particular importance is the inclusion of the heavy chain CDR3 region and, to a lesser extent, the other CDRs of the 8AH8AL, 8AH7AL, 6C, 12C, or 12F antibody, or other anti-B5 or anti-A33 antibody. Such fully human or humanized chimpanzee monoclonal antibodies will have particular utility in that they will not evoke an immune response against the antibody itself.

It is also possible, in accordance with the present invention, to produce chimeric antibodies including non-human sequences. Thus, one may use, for example, murine, ovine, equine, bovine or other mammalian Fc or FR sequences to replace some or all of the Fc or FR regions of the 8AH8AL, 8AH7AL, 6C, 12C, or 12F antibody, or other anti-B5 or anti-A33 antibody. Some of the CDRs may be replaced as well. Again, however, it is preferred that at least the heavy chain CDR3 of the 8AH8AL, 8AH7AL, 6C, 12C, or 12F antibody, or other anti-B5 or anti-A33 antibody be included in such chimeric antibodies and, to a lesser extent, it is also preferred that some or all of the other CDRs of the 8AH8AL, 8AH7AL, 6C, 12C, or 12F antibody, or other anti-B5 or anti-A33 antibody be included. Such chimeric antibodies bearing non-human immunoglobulin sequences admixed with the CDRs of the 8AH8AL, 8AH7AL, 6C, 12C, or 12F antibody, or other anti-B5 or anti-A33 antibody are not preferred for use in humans and are particularly not preferred for extended use because they may evoke an immune response against the non-human sequences. They may, of course, be used for brief periods or in immunosuppressed individuals but, again, fully human or humanized chimpanzee monoclonal antibodies are preferred. Because such antibodies may be used for brief periods or in immunosuppressed subjects, chimeric antibodies bearing non-human mammalian Fc and FR sequences but including at least the heavy chain CDR3 of the 8AH8AL, 8AH7AL, 6C, 12C, or 12F antibody, or other anti-B5 or anti-A33 antibody are contemplated as alternative embodiments of the present invention.

For inoculation or prophylactic uses, the antibodies of the present invention are preferably full-length antibody molecules including the Fc region. Such full-length antibodies will have longer half-lives than smaller fragment antibodies (e.g. Fab) and are more suitable for intravenous, intraperitoneal, intramuscular, intracavity, subcutaneous, or transdermal administration.

In some embodiments, Fab fragments, including chimeric Fab fragments, are preferred. Fabs offer several advantages over F(ab')$_2$ and whole immunoglobulin molecules for this therapeutic modality. First, because Fabs have only one binding site for their cognate antigen, the formation of immune complexes is precluded whereas such complexes can be generated when bivalent F(ab')$_2$ s and whole immunoglobulin molecules encounter their target antigen. This is of some importance because immune complex deposition in tissues can produce adverse inflammatory reactions. Second, because Fabs lack an Fc region they cannot trigger adverse inflammatory reactions that are activated by Fc, such as activation of the complement cascade. Third, the tissue penetration of the small Fab molecule is likely to be much better than that of the larger whole antibody. Fourth, Fabs can be produced easily and inexpensively in bacteria, such as *E. coli*, whereas whole immunoglobulin antibody molecules require mammalian cells for their production in useful amounts. The latter entails transfection of immunoglobulin sequences into mammalian cells with resultant transformation. Amplification of these sequences must then be achieved by rigorous selective procedures and stable transformants must be identified and maintained. The whole immunoglobulin molecules must be produced by stably transformed, high expression mammalian cells in culture with the attendant problems of serum-containing culture medium. In contrast, production of Fabs in *E. coil* eliminates these difficulties and makes it possible to produce these antibody fragments in large fermenters which are less expensive than cell culture-derived products.

In addition to Fabs, smaller antibody fragments and epitope-binding peptides having binding specificity for the epitope defined by the 8AH8AL, 8AH7AL, 6C, 12C, or 12F antibody, or other anti-B5 or anti-A33 antibody are also contemplated by the present invention and can also be used to bind or neutralize the virus. For example, single chain antibodies can be constructed according to the method of U.S. Pat. No. 4,946,778, to Ladner et al. Single chain antibodies comprise the variable regions of the light and heavy chains joined by a flexible linker moiety. Yet smaller is the antibody fragment known as the single domain antibody or Fd, which comprises an isolated VH single domain. Techniques for obtaining a single domain antibody with at least some of the binding specificity of the full-length antibody from which they are derived are known in the art.

It is possible to determine, without undue experimentation, if an altered or chimeric antibody has the same specificity as the 8AH8AL, 8AH7AL, 6C, 12C, or 12F antibody, or other anti-B5 or anti-A33 antibody of the invention by ascertaining whether the former blocks the latter from binding to B5 or A33 antigen. If the monoclonal antibody being tested competes with the 8AH8AL, 8AH7AL, 6C, 12C, or 12F antibody, or other anti-B5 or anti-A33 antibody, as shown by a decrease in binding of the 8AH8AL, 8AH7AL, 6C, 12C, or 12F antibody, or other anti-B5 or anti-A33 antibody, then it is likely that the two monoclonal antibodies bind to the same, or a closely spaced, epitope. Still another way to determine whether a monoclonal antibody has the specificity of the 8AH8AL, 8AH7AL, 6C, 12C, or 12F antibody, or other anti-B5 or anti-A33 antibody of the invention is to pre-incubate the 8AH8AL, 8AH7AL, 6C, 12C, or 12F antibody, or other anti-B5 or anti-A33 antibody with B5 or A33 antigen with which it is normally reactive, and then add the monoclonal antibody being tested to determine if the monoclonal antibody being tested is inhibited in its ability to bind B5 or A33 antigen. If the monoclonal antibody being tested is inhibited then, in all likelihood, it has the same, or a functionally equivalent, epitope and specificity as the 8AH8AL, 8AH7AL, 6C, 12C, or 12F antibody, or other anti-B5 or anti-A33 antibody of the invention. Screening of monoclonal antibodies of the invention also can be carried out utilizing an Orthopoxvirus and determining whether the monoclonal antibody neutralizes the virus.

By using the antibodies of the invention, it is now possible to produce anti-idiotypic antibodies which can be used to screen other monoclonal antibodies to identify whether the antibody has the same binding specificity as an antibody of the invention. In addition, such antiidiotypic antibodies can be used for active immunization (Herlyn, D. et al. 1986 *Science* 232:100-102). Such anti-idiotypic antibodies can be produced using well-known hybridoma techniques (Kohler, G. and Milstein, C. 1975 *Nature* 256:495-497). An anti-idiotypic antibody is an antibody which recognizes unique determinants present on the monoclonal antibody produced by the cell line of interest. These determinants are located in the hypervariable region of the antibody. It is this region which binds to a given epitope and, thus, is responsible for the specificity of the antibody.

An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for the monoclonal antibodies of the invention, it is possible to identify other clones with the same idiotype as the antibody of the hybridoma used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the image of the epitope bound by the first monoclonal antibody. Thus, the anti-idiotypic monoclonal antibody can be used for immunization, since the anti-idiotype monoclonal antibody binding domain effectively acts as an antigen.

Nucleic Acids Encoding Anti-B5 or Anti-A33 Monoclonal Antibodies

Given the disclosure herein of the amino acid sequences of the heavy chain Fd and light chain variable domains of the 8AH8AL, 8AH7AL, 6C, 12C, or 12F antibody, or other anti-B5 or anti-A33 antibody, one of ordinary skill in the art is now enabled to produce nucleic acids which encode these antibodies or which encode the various fragment antibodies or chimeric antibodies described above. It is contemplated that such nucleic acids will be operably joined to other nucleic acids forming a recombinant vector for cloning or for expression of the antibodies of the invention. The present invention includes any recombinant vector containing the coding sequences, or part thereof, whether for prokaryotic or eukaryotic transformation, transfection or gene therapy. Such vectors may be prepared using conventional molecular biology techniques, known to those with skill in the art, and would comprise DNA coding sequences for the immunoglobulin V-regions of the 8AH8AL, 8AH7AL, 6C, 12C, or 12F antibody, or other anti-B5 or anti-A33 antibody, including framework and CDRs or parts thereof, and a suitable promoter either with (Whittle, N. et al. 1987 *Protein Eng.* 1:499-505 and Burton, D. R. et al. 1994 *Science* 266:1024-1027) or without (Marasco, W. A. et al. 1993 *Proc. Natl. Acad, Sci.* (*USA*) 90:7889-7893 and Duan, L. et al. 1994 *Proc. Natl. Acad, Sci.* (*USA*) 91:5075-5079) a signal sequence for export or secretion. Such vectors may be transformed or transfected into prokaryotic (Huse, W. D. et al. 1989 *Science* 246:1275-1281; Ward, S. et al. 1989 *Nature* 341:544-546; Marks, J. D. et al. 1991 *J Mol. Biol.* 222:581-597; and Barbas, C. F. et al. 1991 *Proc. Natl. Acad. Sci.* (*USA*) 88:7978-7982) or eukaryotic (Whittle, N. et al. 1987 *Protein Eng.* 1:499-505 and Burton, D. R. et al. 1994 *Science* 266:1024-1027) cells or used for gene therapy (Marasco, W. A. et al. 1993 *Proc. Natl. Acad, Sci.* (*USA*) 90:7889-7893 and Duan, L. et al. 1994 *Proc. Natl. Acad, Sci.* (*USA*) 91:5075-5079) by conventional techniques, known to those with skill in the art.

The expression vectors of the present invention include regulatory sequences operably joined to a nucleotide sequence encoding one of the antibodies of the invention. As used herein, the term "regulatory sequences" means nucleotide sequences which are necessary for or conducive to the transcription of a nucleotide sequence which encodes a desired polypeptide and/or which are necessary for or conducive to the translation of the resulting transcript into the desired polypeptide. Regulatory sequences include, but are not limited to, 5' sequences such as operators, promoters and ribosome binding sequences, and 3' sequences such as polyadenylation signals. The vectors of the invention may optionally include 5' leader or signal sequences, 5' or 3' sequences encoding fusion products to aid in protein purification, and various markers which aid in the identification or selection of transformants. The choice and design of an appropriate vector is within the ability and discretion of one of ordinary skill in the art. The subsequent purification of the antibodies may be accomplished by any of a variety of standard means known in the art.

A preferred vector for screening monoclonal antibodies, but not necessarily preferred for the mass production of the antibodies of the invention, is a recombinant DNA molecule containing a nucleotide sequence that codes for and is capable of expressing a fusion polypeptide containing, in the direction of amino- to carboxy-terminus, (1) a prokaryotic secretion signal domain, (2) a polypeptide of the invention, and, optionally, (3) a fusion protein domain. The vector includes DNA regulatory sequences for expressing the fusion polypeptide, preferably prokaryotic, regulatory sequences. Such vectors can be constructed by those with skill in the art and have been described by Smith, G. P. et al. (1985 *Science* 228:1315-1317); Clackson, T. et al. (1991 *Nature* 352:624-628); Kang et al. (1991 in "Methods: A Companion to Methods in Enzymology: Vol. 2"; R. A. Lerner and D. R. Burton, ed. Academic Press, NY, pp 111-118); Barbas, C. F. et al. (1991 *Proc, Natl. Acad. Sci, (USA)* 88:7978-7982), Roberts, B. L. et al. (1992 *Proc. Natl. Acad. Sci. (USA)* 89:2429-2433).

A fusion polypeptide may be useful for purification of the antibodies of the invention. The fusion domain may, for example, include a poly-His tail which allows for purification on Ni+ columns or the maltose binding protein of the commercially available vector pMAL (New England BioLabs, Beverly, Mass.). A currently preferred, but by no means necessary, fusion domain is a filamentous phage membrane anchor. This domain is particularly useful for screening phage display libraries of monoclonal antibodies but may be of less utility for the mass production of antibodies. The filamentous phage membrane anchor is preferably a domain of the cpIII or cpVIII coat protein capable of associating with the matrix of a filamentous phage particle, thereby incorporating the fusion polypeptide onto the phage surface, to enable solid phase binding to specific antigens or epitopes and thereby allow enrichment and selection of the specific antibodies or fragments encoded by the phagemid vector.

The secretion signal is a leader peptide domain of a protein that targets the protein to the membrane of the host cell, such as the periplasmic membrane of Gram-negative bacteria. The leader sequence of the pelB protein has previously been used as a secretion signal for fusion proteins (Better, M. et al. 1988 *Science* 240:1041-1043; Sastry, L. et al. 1989 *Proc, Natl. Acad. Sci (USA)* 86:5728-5732; and Mullinax, R. L. et al., 1990 *Proc. Natl. Acad. Sci. (USA)* 87:8095-8099). Amino acid residue sequences for other secretion signal polypeptide domains from *E. coli* useful in this invention can be found in Neidhard, F. C. (ed.), 1987 *Escherichia coli and Salmonella Typhimurium: Typhimurium Cellular and Molecular Biology*, American Society for Microbiology, Washington, D.C.

To achieve high levels of gene expression in *E. coli*, it is necessary to use not only strong promoters to generate large quantities of mRNA, but also ribosome binding sites to ensure that the mRNA is efficiently translated. In *E. coli*, the ribosome binding site includes an initiation codon (AUG) and a sequence 3-9 nucleotides long located 3-11 nucleotides upstream from the initiation codon (Shine et al. 1975 *Nature* 254:34-38). The sequence, which is called the Shine-Dalgarno (SD) sequence, is complementary to the 3' end of *E. coli* 16S rRNA. Binding of the ribosome to mRNA and the sequence at the 3' end of the mRNA can be affected by several factors: the degree of complementarity between the SD sequence and 3' end of the 16S rRNA; the spacing lying between the SD sequence and the AUG; and the nucleotide sequence following the AUG, which affects ribosome binding. The 3' regulatory sequences define at least one termination (stop) codon in frame with and operably joined to the heterologous fusion polypeptide.

In preferred embodiments with a prokaryotic expression host, the vector utilized includes a prokaryotic origin of replication or replicon, i.e., a DNA sequence having the ability to direct autonomous replication and maintenance of the recombinant DNA molecule extrachromosomally in a prokaryotic host cell, such as a bacterial host cell, transformed therewith. Such origins of replication are well known in the art. Preferred origins of replication are those that are efficient in the host organism. A preferred host cell is *E. coli*. For use of a vector in *E. coli*, a preferred origin of replication is ColEI found in pBR322 and a variety of other common plasmids. Also preferred is the p15A origin of replication found on pACYC and its derivatives. The ColEI and p15A replicons have been extensively utilized in molecular biology and are available on a variety of plasmids and are described by Sambrook et al., 1989, *Molecular Cloning: A Laboratory Manual*, 2nd edition, Cold Spring Harbor Laboratory Press.

In addition, those embodiments that include a prokaryotic replicon preferably also include a gene whose expression confers a selective advantage, such as drug resistance, to a bacterial host transformed therewith. Typical bacterial drug resistance genes are those that confer resistance to ampicillin, tetracycline, neomycin/kanamycin or chloramphenicol. Vectors typically also contain convenient restriction sites for insertion of translatable DNA sequences. Exemplary vectors are the plasmids pUC18 and pUC19 and derived vectors such as those commercially available from suppliers such as Invitrogen, (San Diego, Calif.).

When the antibodies of the invention include both heavy chain and light chain sequences, these sequences may be encoded on separate vectors or, more conveniently, may be expressed by a single vector. The heavy and light chain may, after translation or after secretion, form the heterodimeric structure of natural antibody molecules. Such a heterodimeric antibody may or may not be stabilized by disulfide bonds between the heavy and light chains.

A vector for expression of heterodimeric antibodies, such as the full-length antibodies of the invention or the F(ab')$_2$, Fab or Fv fragment antibodies of the invention, is a recombinant DNA molecule adapted for receiving and expressing translatable first and second DNA sequences. That is, a DNA expression vector for expressing a heterodimeric antibody provides a system for independently cloning (inserting) the two translatable DNA sequences into two separate cassettes present in the vector, to form two separate cistrons for expressing the first and second polypeptides of a heterodimeric antibody. The DNA expression vector for expressing two cistrons is referred to as a di-cistronic expression vector.

Preferably, the vector comprises a first cassette that includes upstream and downstream DNA regulatory sequences operably joined via a sequence of nucleotides adapted for directional ligation to an insert DNA. The upstream translatable sequence preferably encodes the secretion signal as described above. The cassette includes DNA regulatory sequences for expressing the first antibody polypeptide that is produced when an insert translatable DNA sequence (insert DNA) is directionally inserted into the cassette via the sequence of nucleotides adapted for directional ligation.

The dicistronic expression vector also contains a second cassette for expressing the second antibody polypeptide. The second cassette includes a second translatable DNA sequence that preferably encodes a secretion signal, as described above, operably joined at its 3' terminus via a sequence of nucleotides adapted for directional ligation to a downstream DNA sequence of the vector that typically defines at least one stop codon in the reading frame of the cassette. The second translatable DNA sequence is operably joined at its 5' terminus to DNA regulatory sequences forming the 5' elements. The second cassette is capable, upon insertion of a translatable DNA sequence (insert DNA), of expressing the second fusion polypeptide comprising a secretion signal with a polypeptide coded by the insert DNA.

The antibodies of the present invention may additionally, of course, be produced by eukaryotic cells such as CHO cells, human or mouse hybridomas, immortalized B-lymphoblastoid cells, and the like. In this case, a vector is constructed in which eukaryotic regulatory sequences are operably joined to the nucleotide sequences encoding the antibody polypeptide or polypeptides. The design and selection of an appropriate eukaryotic vector is within the ability and discretion of one of ordinary skill in the art. The subsequent purification of the antibodies may be accomplished by any of a variety of standard means known in the art.

The antibodies of the present invention may furthermore, of course, be produced in plants. In 1989, Hiatt et al. 1989, *Nature* 342:76-78 first demonstrated that functional antibodies could be produced in transgenic plants. Since then, a considerable amount of effort has been invested in developing plants for antibody (or "plantibody") production (for reviews see Giddings, G. et al., 2000 *Nat Biotechnol* 18:1151-1155; Fischer, R. and Emans, N., 2000, *Transgenic Res* 9:279-299). Recombinant antibodies can be targeted to seeds, tubers, or fruits, making administration of antibodies in such plant tissues advantageous for immunization programs in developing countries and worldwide.

In another embodiment, the present invention provides host cells, both prokaryotic and eukaryotic, transformed or transfected with, and therefore including, the vectors of the present invention.

Diagnostic and Pharmaceutical Anti-B5 or Anti-A33 Monoclonal Antibody Preparations The invention also relates to a method for preparing diagnostic or pharmaceutical compositions comprising the monoclonal antibodies of the invention or polynucleotide sequences encoding the antibodies of the invention or part thereof, the pharmaceutical compositions being used for immunoprophylaxis or immunotherapy of Orthopoxvirus infection. The pharmaceutical preparation includes a pharmaceutically acceptable carrier. Such carriers, as used herein, means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

A preferred embodiment of the invention relates to monoclonal antibodies whose heavy chains comprise in CDR3 the polypeptide having SEQ ID NO: 7, and/or whose light chains comprise in CDR3 the polypeptide having SEQ ID NO: 15; whose heavy chains comprise in CDR3 the polypeptide having SEQ ID NO: 23, and/or whose light chains comprise in CDR3 the polypeptide having SEQ ID NO: 31; whose heavy chains comprise in CDR3 the polypeptide having SEQ ID NO: 39, and/or whose light chains comprise in CDR3 the polypeptide having SEQ ID NO: 47; whose heavy chains comprise in CDR3 the polypeptide having SEQ ID NO: 55, and/or whose light chains comprise in CDR3 the polypeptide having SEQ ID NO: 63; whose heavy chains comprise in CDR3 the polypeptide having SEQ ID NO: 71, and/or whose light chains comprise in CDR3 the polypeptide having SEQ ID NO: 79; and conservative variations of these peptides. The term "conservative variation" as used herein denotes the replacement of an amino acid residue by another, biologically similar residue. Examples of conservative variations include the substitution of one hydrophobic residue such as isoleucine, valine, leucine or methionine for another or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies having the substituted polypeptide also bind or neutralize an Orthopoxvirus. Analogously, another preferred embodiment of the invention relates to polynucleotides which encode the above noted heavy chain polypeptides and to polynucleotide sequences which are complementary to these polynucleotide sequences. Complementary polynucleotide sequences include those sequences that hybridize to the polynucleotide sequences of the invention under stringent hybridization conditions.

The 8AH8AL, 8AH7AL, 6C, 12C, or 12F antibody, or other anti-B5 or anti-A33 antibody of the invention may be labeled by a variety of means for use in diagnostic and/or pharmaceutical applications. There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

Another labeling technique which may result in greater sensitivity consists of coupling the antibodies to low molecular weight haptens. These haptens can then be specifically altered by means of a second reaction. For example, it is common to use haptens such as biotin, which reacts with avidin, or dinitrophenol, pyridoxal, or fluorescein, which can react with specific antihapten antibodies.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a monoclonal antibody of the invention that is, or can be, detectably labeled. The kit may also have containers containing buffer(s) and/or a container comprising a reporter-means, such as a biotin-binding protein, such as avidin or streptavidin, bound to a reporter molecule, such as an enzymatic or fluorescent label.

In Vitro Detection and Diagnostics

The monoclonal antibodies of the invention are suited for in vitro use, for example, in immunoassays in which they can be utilized in liquid phase or bound to a solid phase carrier. In addition, the monoclonal antibodies in these immunoassays can be detectably labeled in various ways. Examples of types of immunoassays which can utilize the monoclonal antibodies of the invention are competitive and non-competitive immunoassays in either a direct or indirect format. Examples of such immunoassays are the radioimmunoassay (RIA) and the sandwich (immunometric) assay. Detection of antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of Orthopoxvirus. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble for purposes of the invention. Those skilled in the art will know of other suitable carriers for binding monoclonal antibodies, or will be able to ascertain such, using routine experimentation.

For purposes of the invention, Orthopoxvirus may be detected by the monoclonal antibodies of the invention when present in biological fluids and tissues. Any sample containing a detectable amount of Orthopoxvirus can be used. A sample can be a liquid such as urine, saliva, cerebrospinal fluid, blood, serum or the like; a solid or semi-solid such as tissues, feces, or the like; or, alternatively, a solid tissue such as those commonly used in histological diagnosis.

In Vivo Detection of Orthopoxvirus

In using the monoclonal antibodies of the invention for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the B5 or A33 antigen for which the monoclonal antibodies are specific.

The concentration of detectably labeled monoclonal antibody which is administered should be sufficient such that the binding to Orthopoxvirus is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of infection of the individual. The dosage of monoclonal antibody can vary from about 0.01 mg/kg to about 50 mg/kg, preferably 0.1 mg/kg to about 20 mg/kg, most preferably about 0.1 mg/kg to about 5 mg/kg. Such dosages may vary, for example, depending on whether multiple injections are given, on the tissue being assayed, and other factors known to those of skill in the art.

For in vivo diagnostic imaging, the type of detection instrument available is a major factor in selecting an appropriate radioisotope. The radioisotope chosen must have a type of decay which is detectable for the given type of instrument. Still another important factor in selecting a radioisotope for in vivo diagnosis is that the half-life of the radioisotope be long enough such that it is still detectable at the time of maximum uptake by the target, but short enough such that deleterious radiation with respect to the host is acceptable. Ideally, a radioisotope used for in vivo imaging will lack a particle emission but produce a large number of photons in the 140-250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions are the bifunctional chelating agents such as diethylenetriaminepentacetic acid (DTPA) and ethylenediaminetetra-acetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr and $^{56}$Fe.

The monoclonal antibodies of the invention can be used in vitro and in vivo to monitor the course of Orthopoxvirus infection therapy. Thus, for example, by measuring the increase or decrease in the number of cells infected with Orthopoxvirus or changes in the concentration of Orthopoxvirus present in the body or in various body fluids, it would be possible to determine whether a particular therapeutic regimen aimed at ameliorating Orthopoxvirus infection is effective.

Prophylaxis and Therapy of Orthopoxvirus Infection

The monoclonal antibodies can also be used in prophylaxis and as therapy for Orthopoxvirus infection in humans or other animals. The terms, "prophylaxis" and "therapy" as used herein in conjunction with the monoclonal antibodies of the invention denote both prophylactic as well as therapeutic administration and both passive immunization with substantially purified polypeptide products, as well as gene therapy by transfer of polynucleotide sequences encoding the product or part thereof. Thus, the monoclonal antibodies can be administered to high-risk subjects in order to lessen the likelihood and/or severity of Orthopoxvirus infection or administered to subjects already evidencing active Orthopoxvirus infection. In the present invention, Fab fragments also bind or neutralize Orthopoxviruses and therefore may be used to treat Orthopoxvirus infection but full-length antibody molecules are otherwise preferred.

As used herein, a "prophylactically effective amount" of the monoclonal antibodies of the invention is a dosage large enough to produce the desired effect in the protection of individuals against Orthopoxvirus infection for a reasonable period of time, such as one to two months or longer following administration. A prophylactically effective amount is not, however, a dosage so large as to cause adverse side effects, such as hyperviscosity syndromes, pulmonary edema, congestive heart failure, and the like. Generally, a prophylactically effective amount may vary with the subject's age, condition, and sex, as well as the extent of the infection in the subject and can be determined by one of skill in the art. The dosage of the prophylactically effective amount may be adjusted by the individual physician or veterinarian in the event of any complication. A prophylactically effective amount may vary from about 0.01 mg/kg to about 50 mg/kg, preferably from about 0.1 mg/kg to about 20 mg/kg, most preferably from about 0.2 mg/kg to about 5 mg/kg, in one or more administrations (priming and boosting).

As used herein, a "therapeutically effective amount" of the monoclonal antibodies of the invention is a dosage large enough to produce the desired effect in which the symptoms of Orthopoxvirus infection are ameliorated or the likelihood of infection is decreased. A therapeutically effective amount is not, however, a dosage so large as to cause adverse side effects, such as hyperviscosity syndromes, pulmonary edema, congestive heart failure, and the like. Generally, a therapeutically effective amount may vary with the subject's age, condition, and sex, as well as the extent of the infection in the subject and can be determined by one of skill in the art. The dosage of the therapeutically effective amount may be adjusted by the individual physician or veterinarian in the event of any complication. A therapeutically effective amount may vary from about 0.01 mg/kg to about 50 mg/kg, preferably from about 0.1 mg/kg to about 20 mg/kg, most preferably from about 0.2 mg/kg to about 5 mg/kg, in one or more dose administrations daily, for one or several days. Preferred is administration of the antibody for 2 to 5 or more consecutive days in order to avoid "rebound" of virus replication from occurring.

The monoclonal antibodies of the invention can be administered by injection or by gradual infusion over time. The administration of the monoclonal antibodies of the invention may, for example, be intravenous, intraperitoneal, intramuscular, intracavity, subcutaneous, or transdermal. Techniques for preparing injectate or infusate delivery systems containing antibodies are well known to those of skill in the art. Generally, such systems should utilize components which will not significantly impair the biological properties of the antibodies, such as the paratope binding capacity (see, for example, *Remington's Pharmaceutical Sciences*, 18th edition, 1990, Mack Publishing). Those of skill in the art can readily determine the various parameters and conditions for producing antibody injectates or infusates without resort to undue experimentation.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and the like.

Chimpanzee Monoclonal Antibodies to Vaccinia Virus B5 Protein Protect Mice Against Vaccinia Virus and Neutralize Vaccinia and Smallpox Viruses Chimpanzee Fabs against the B5 envelope glycoprotein of vaccinia virus were isolated and converted into complete monoclonal antibodies (MAbs) with human γ1 heavy chain constant regions. The two MAbs (8AH8AL and 8AH7AL) displayed high binding affinities to B5 ($K_d$ of 0.2 nM and 0.7 nM). The MAb 8AH8AL inhibited the spread of vaccinia virus as well as variola virus (the causative agent of smallpox) in vitro, protected mice from subsequent intranasal challenge with virulent vaccinia virus, protected mice when administered 2 days post-challenge and provided significantly greater protection than that afforded by a previously isolated rat anti-B5 MAb (19C2) or by vaccinia immune globulin. The MAb bound to a conformational epitope between amino acids 20 and 130 of B5. These chimpanzee/human anti-B5 MAbs are envisioned as providing the basis for the prevention and treatment of vaccinia virus-induced complications of vaccination against smallpox and in the immunoprophylaxis and immunotherapy of smallpox.

Isolation and Characterization of Vaccinia B5-Specific Fabs

The chimpanzee Fab-displaying phage library was panned against recombinant VACV B5 protein (275t) and 96 individual clones were randomly picked and screened for binding to B5 by phage ELISA with BSA as a negative control. Ninety percent of the clones preferentially bound to B5. DNA sequencing of the variable regions of heavy (VH) and light (VL) chains from 18 positive clones showed that a single VH gene was paired with two different VL genes. These two clones were designated 8AH8AL and 8AH7AL (GenBank accession numbers: DQ316791, DQ316789, DQ316792, and DQ316790). The sequences of VH and VL genes are shown in FIGS. 1a and 1b. A search in V-Base (Cook, G. P. & Tomlinson, I. M. 1995 *Immunol Today* 16:237-242) indicated that the VH gene putatively originated from germline gene V3-49, which belongs to the VH3 family; the two VL genes were from Vλ germline gene 2a2.272A12, which belongs to the Vλ 2 family.

The Fab sequences were converted into full-length IgG as described in Example 1 and the IgGs were examined for their binding specificity by ELISA. Anti-B5 8AH8AL bound to B5 protein with high specificity and affinity, but not to unrelated proteins (BSA, thyroglobulin, phosphorylase b, lysozyme and cytochrome-c) (FIG. 1c). The two anti-B5 MAbs had the identical binding specificity.

Epitope Recognized by the Anti-B5 Mab

In the absence of differences in heavy chain sequence, 8AH8AL was chosen for epitope mapping as it had a slightly higher affinity. Western blotting was used to locate the epitope recognized by anti-B5 8AH8AL. Different B5 fragments generated by N- and C-terminal deletions were produced in bacteria. Western blotting with anti-His confirmed that similar amounts of each peptide were tested for reaction with anti-B5 8AH8AL. As seen in FIG. 2a and summarized in FIG. 2b, the shortest peptide that strongly reacted with anti-B5 8AH8AL consisted of residues 20 to 130 on B5 protein. Therefore, it required 110 amino acid residues to form the epitope, which suggested the epitope was conformational since a linear epitope is usually composed of 5-15 amino acid residues.

To address whether MAbs can react with its smallpox B5 counterpart, the B520-130 protein of VACV was converted to that of variola virus via splicing by overlap extension PCR (Example 5). Vaccinia and variola virus B520-130 proteins were quantified by Western blotting using HRP-conjugated anti-His. The Western blotting with 8AH8AL showed that anti-B5 MAb cross-reacted with smallpox B520-130, although the reaction was not as strong as with VACV B520-130.

Binding Affinity and In Vitro Neutralizing Activity

The affinity of the two chimpanzee/human MAbs and a rat MAb (19C2) for binding to VACV B5 protein was measured by surface plasmon resonance (SPR) biosensor. A $K_d$ of 0.6 nM and a dissociation rate constant of $\sim 10^{-5}$/sec was observed for 8AH8AL (Table 1). A similar $K_d$ was determined in the SPR solution competition assay, both for 8AH8AL (0.2 nM) and for 8AH7AL (0.7 nM). In contrast, the affinity of the rat MAb 19C2 was ~13-fold weaker (Table 1). Remarkably, the off-rate of the MAb 8AH8AL was 25-fold slower than that of the rat MAb 19C2. Thus, the half life of the antibody-antigen complex was ~19 h for the chimpanzee/human MAbs and less than 45 min for the rat MAb.

TABLE 1

Antibody affinity of anti-B5 Mabs[1]

| Antibody | $k_{on}$ (M$^{-1}$s$^{-1}$) | $k_{off}$ (s$^{-1}$) | $K_d$ (nM) |
|---|---|---|---|
| 8AH8AL | $2 \times 10^4$ | $1 \times 10^{-5}$ | 0.6 |
| 19C2 | $3 \times 10^4$ | $2.6 \times 10^{-4}$ | 7.5 |

[1]Anti-B5 IgG of chimpanzee/human MAb 8AH8AL and a rat MAb 19C2 were immobilized individually on the surface plasmon resonance sensor surfaces. The antibody binding responses to B5 (275t) protein were collected at a range of concentrations between 0.05 and 500 nM of antigen. The kinetic rate constant of association ($k_{on}$) and dissociation ($k_{off}$) rates were measured from surface binding kinetics, and the equilibrium dissociation constant ($K_d$) was calculated as the ratio $k_{off}/k_{on}$.

Figure 3:
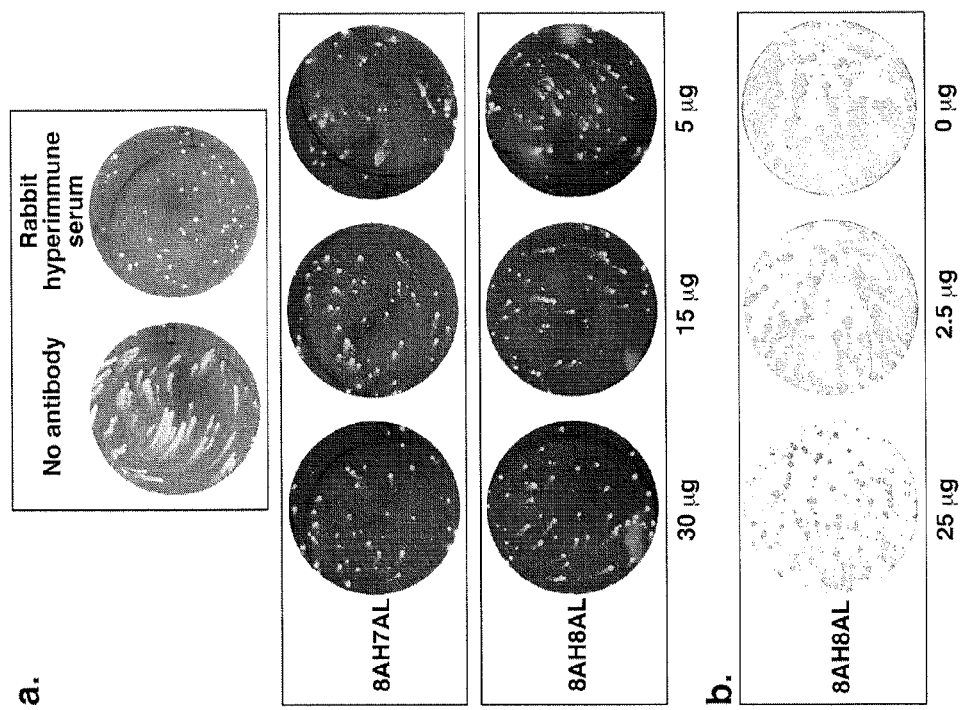
FIG. 3. In vitro neutralizing activity of anti-B5 MAbs, measured by a comet-reduction assay. (a), BS-C-1 cells were infected with approximately 50 plaque-forming units of VACV, strain IHD-J. After 2 h at 37° C., the monolayer was washed and fresh medium containing indicated amounts of chimpanzee anti-BS 8AH7AL or 8AH8AL was added. PBS and rabbit hyper-immune serum served as negative and positive controls, respectively. After 48 h, the monolayers were stained with crystal violet. For the smallpox assay (b), monolayers of BS-C-40 cells in 6-well cell culture plates were infected with the Solaimen strain of variola virus at 50 plaque-forming units per well in RPMI medium containing 2% FBS. After 1 h, the medium was aspirated; cells were washed twice, and overlaid with RPMI containing 25 µg, 2.5 µg, or 0 µg of anti-B5 IgG. The plates were then incubated in a CO$_2$ incubator for 4 days at 35.5° C. Cells were fixed and reacted with polyclonal rabbit anti-variola virus antibody. Following incubation with goat anti-rabbit-HRP conjugate, comets were visualized by addition of TruBlue peroxidase substrate.

Since B5 is an EV-specific protein, in vitro neutralization activity of anti-B5 MAbs was measured by the comet-reduction assay, an established method that measures the inhibition of comet-like plaque formation by the released EV form of the virus (Appleyard, G. et al. 1971 *J Gen Virol* 13:9-17; Law, M. et al. 2002 *J Gen Virol* 83:209-222). The EV of the IHD strain of VACV formed comet-shaped plaques in the absence of antibodies, but the formation of comets was completely blocked by the addition of an excess of rabbit hyperimmune serum to VACV (FIG. 3a). The monoclonal anti-B5 clones, 8AH8AL and 8AH7AL, reduced the formation of comet-like plaques of vaccinia virus EV at the lowest dose tested (FIG. 3a). Similarly, the formation of comet-shaped plaques of the Solaimen strain of variola EV was inhibited by 8AH8AL in a dose-dependent manner (FIG. 3b), indicating that the anti-B5 MAbs possessed neutralizing activity against EV of both viruses.

Protection of Mice Against Challenge with Virulent VACV

Figure 4:
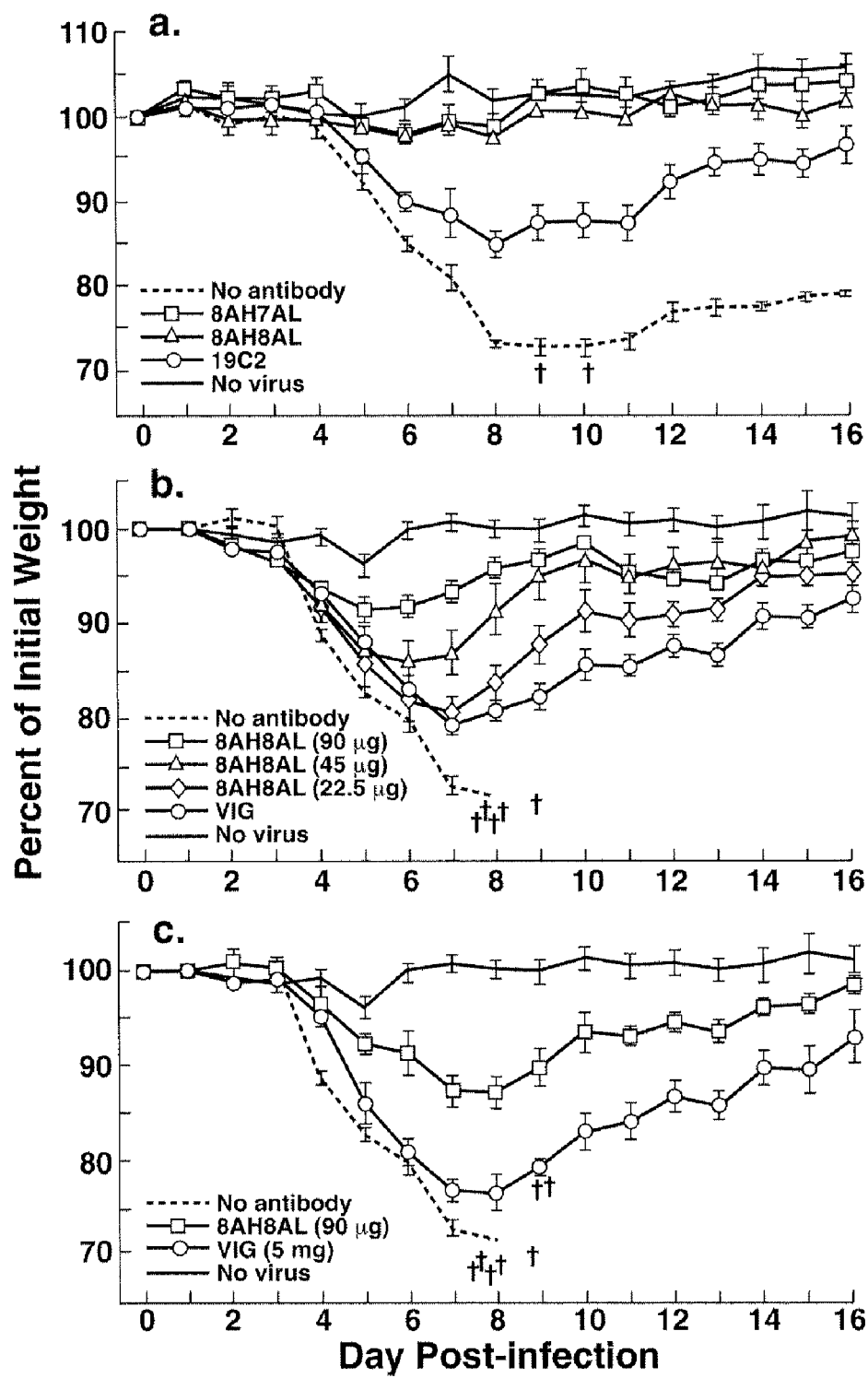
FIG. 4. Prophylactic and therapeutic protection in mice by anti-B5 MAbs. Groups of five BALB/c mice were inoculated intraperitoneally with 90 µg of purified IgG (a), or different amounts of IgG (b). Twenty four hours later, mice were challenged intranasally with $10^5$ plaque-forming units (pfu) of the WR strain of vaccinia virus. Ninety micrograms of rat anti-B5 19C2 IgG (a) or 5 mg of human vaccinia immune globulin (VIG) (b) were used for comparison. (c) Groups of five BALB/c mice were inoculated intranasally with $10^5$ pfu of vaccinia virus, strain WR. After 48 h, the mice were injected intraperitoneally with 90 µg of purified IgG, or 5 mg of human VIG. Mice were weighed individually and mean percentages of starting weight±standard error were plotted. Controls were unimmunized (no antibody) or unchallenged (no virus). †, died naturally or killed because of 30% weight loss.

The BALB/c mouse pneumonia model with VACV WR challenge (Smee, D. F. et al. 2001 *Antiviral Res* 52:55-62; Williamson, J. D. et al. 1990 *J Gen Virol* 71:2761-2767) was used for the following reasons: weight loss and death are correlated with replication in the lungs, allowing the onset and progress of disease to be monitored by a non-invasive method that reduces the number of animals needed for significance (Law, M. et al. 2005 *J Gen Virol* 86:991-1000); the model has been used for active immunization studies with live VACV as well as with individual VACV proteins (Fogg, C. et al. 2004 *J Virol* 78:10230-10237) and for passive immunization studies with antisera prepared against VACV and VACV proteins (Law, M. et al. 2005 *J Gen Virol* 86:991-1000), and the intranasal (IN) route is believed to be the major avenue for transmission of variola virus. The two anti-B5 chimpanzee/human MAbs, 8AH8AL, 8AH7AL, and a rat anti-B5 MAb, 19C2 (Schmelz, M. et al. 1994 *J Virol* 68:130-147) were compared for their in vivo protective activity. The control mice lost weight continuously starting at day 5 following challenge with $10^5$ pfu of WR and 2 of the 5 mice were sacrificed because they reached 70% of starting weight (FIG. 4a). In contrast, the mice that were injected with MAbs 8AH8AL or 8AH7AL did not lose weight after the identical challenge with $10^5$ pfu of WR, indicating that full protection was achieved. Although the rat MAb 19C2 also protected mice compared to the control mice, substantial weight loss was observed. The two chimpanzee/human MAbs provided significantly better protection than that provided by the rat MAb (P<0.0001 on day 8). The difference in weight loss between the no antibody control group and each of the immunized groups was also highly significant on day 8 (P<0.0001).

Since there was no difference in protective efficiency between 8AH8AL and 8AH7AL, only the 8AH8AL MAb was used in determining the minimum effective dose of anti-B5. The half-life of the MAb was found to be 6.4 days in mice. Groups of mice were given decreasing doses of 8AH8AL (90, 45, 22.5 µg per mouse) and a single 5 mg dose of human VIG (2.5× the recommended human dose on a weight basis) was used for comparison. All 5 control mice died or were sacrificed when their weight fell to 70% of starting weight (FIG. 4b). In contrast, all of the mice injected with 8AH8AL, even at the lowest dose, or with VIG were protected from death following WR challenge. Protection against disease, as measured by the degree of weight loss, however, was dose-dependent for 8AH8AL. The difference in weight loss between mice immunized with 8AH8AL and unimmunized control mice was highly significant on day 7 (P<0.0001 for 90 and 45 µg, P=0.0005 for 22.5 µg). Five mg of VIG reduced weight loss after challenge (P=0.003 on day 7). The difference in weight loss between mice receiving 5 mg of VIG and those receiving 45 µg or 90 µg of 8AH8AL was highly significant on day 8 (P<0.0001). No statistically significant difference was found between 5 mg of VIG and 22.5 µg of 8AH8AL.

The therapeutic value of 8AH8AL was assessed by administration of the MAb two days after challenge with VACV (FIG. 4c). A single 90 µg dose of 8AH8AL administered 48 h after infection protected the mice (P<0.0001 on day 7, versus unimmunized controls) and they experienced only slight weight loss, followed by rapid recovery. In contrast, a single 5 mg dose of VIG administered 48 h after infection afforded much less protection (P=0.057 on day 7, versus unimmunized controls) and 2 of the 5 mice were sacrificed because their weight loss reached 30%. The difference in weight loss between the mice receiving the MAb and those receiving VIG was highly significant on day 7 (P<0.0001), indicating that the MAb was more therapeutic than the VIG.

Convalescent sera collected 22 days after challenge from the mice described above (FIGS. 4b and c) contained negligible amounts of the injected MAbs and were assayed for induced murine antibodies to two EV-associated proteins, B5 and A33, and two MV-associated proteins, L1 and A27, by ELISA The sera were also assayed for neutralizing antibodies to the MV form of VACV. Only challenged mice that had received antibodies (MAb or VIG) were included since all of the non-immunized challenged mice had been sacrificed because of weight loss. Sera from mice not challenged with VACV served as negative controls.

Figure 5:
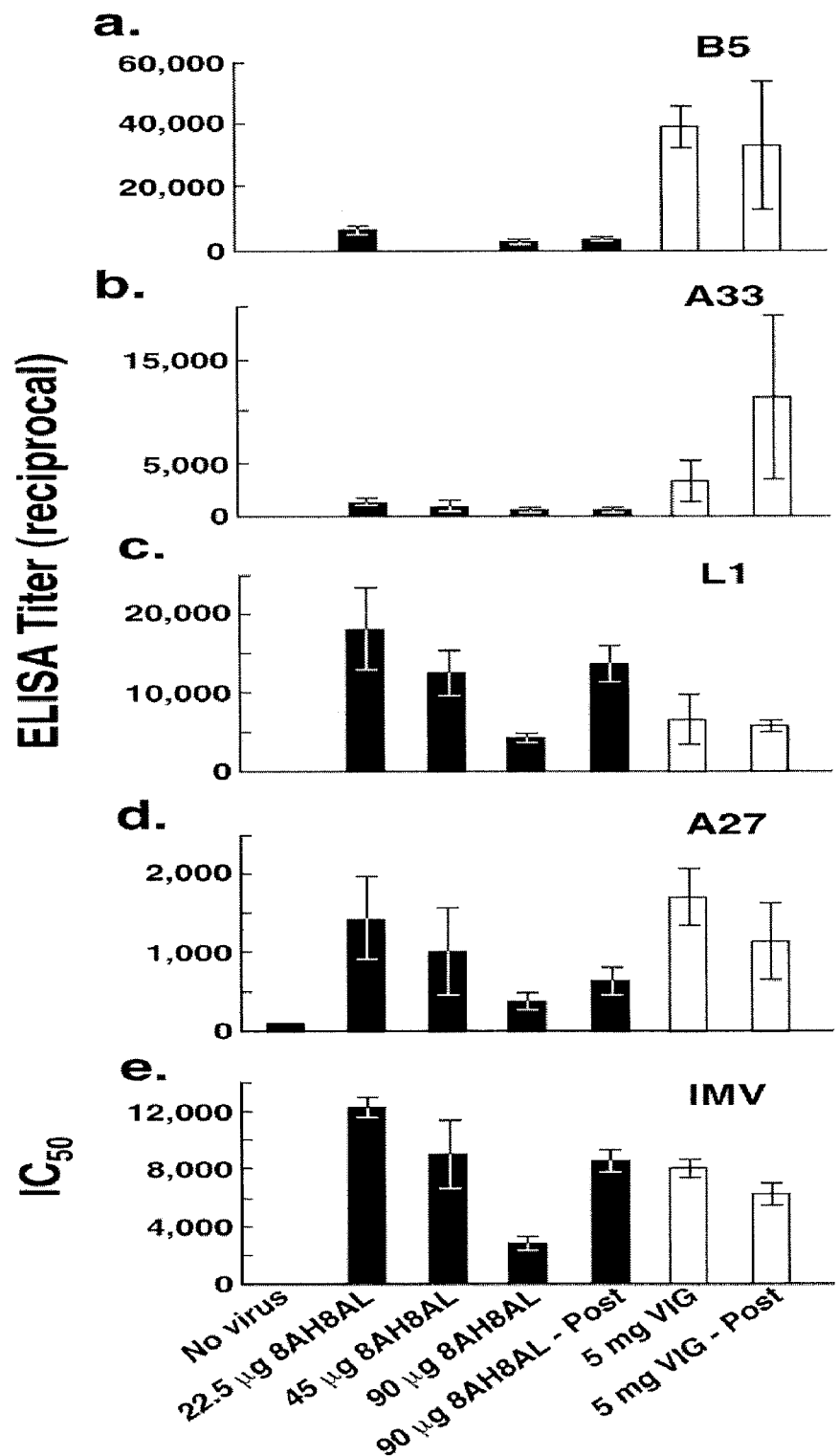
FIG. 5. Antibody responses elicited by challenge with the WR strain of VACV. Mice were bled 22 days after challenge with WR. Individual sera were assayed for binding to EV-associated proteins: B5 (a), and A33 (b); and two MV-associated proteins: L1 (c) and A27 (d). The sera were also assayed for neutralizing antibodies to MV (e). IC$_{50}$: the reciprocal serum dilution that can neutralize 50% of virus. Reciprocal endpoint binding titers were determined by ELISA using anti-mouse peroxidase. Filled and open bars represent animals immunized with 8AH8AL and VIG, respectively. Those groups that received post-exposure immunization are indicated by "-post".

Mice that had received VIG either before or after challenge mounted a significant antibody response against all of the proteins tested (FIG. 5a-d), indicating that viral replication and production of VACV had occurred. In contrast, mice that had received the chimpanzee-derived MAb did not mount a significant immune response to either of the two EV membrane proteins, however, they did demonstrate an immune response to both MV membrane-associated proteins, which varied according to the dose and time of MAb administered, suggesting that higher doses of the MAb inhibited virus replication better than lower doses. This dose-dependent pattern of response by the challenged mice was reflected also in their neutralizing antibody response to MV (FIG. 5e).

Discussion

Several studies have suggested that antibodies are sufficient to protect against orthopoxvirus infections in mice and monkeys (Lustig, S. et al. 2005 *J Virol* 79:13454-13462; Wyatt, L. S. et al. 2004 *Proc Natl Acad Sci USA* 101:4590-4595; Edghill-Smith, Y. et al. 2005 *Nat Med* 11:740-747). Here, we demonstrate that chimpanzee MAbs against VACV B5 protein (an EV-specific protein) alone are sufficient not only to protect mice from lethal challenge with virulent VACV, but also to confer therapeutic protection of mice when administered two days after infection. The result is consistent with the previous finding that neutralizing antibodies against EV play a critical role in protective immunity (Appleyard, G. & Andrews, C. 1974 *J Gen Virol* 23:197-200; Turner, G. S. & Squires, E. J. 1971 *J Gen Virol* 13:19-25).

Our anti-B5 MAbs exhibited much higher protective efficacy than did a rat anti-B5 MAb or human VIG. Competition ELISA showed that chimpanzee/human and rat MAbs did not compete with each other for binding to B5, suggesting that they recognize different epitopes. In addition, the chimpanzee/human MAbs had higher binding affinity than the rat MAb. Noteworthy is that the chimpanzee/human MAbs had a 25-fold slower off-rate than the rat MAb. The difference in binding sites and affinities between the chimpanzee and rat MAbs may contribute to their different protective efficacies. The likely reason that human VIG is inferior to the chimpanzee/human MAbs in animal studies is that the concentration of protective antibodies in VIG is low. Indeed, based on ELISA, we found that 5 mg of VIG contained the equivalent of less than 10 μg of MAb to B5.

The MAbs to B5 inhibited VACV spread in tissue culture cells and their effect in vivo could have a related explanation. We measured mouse antibodies to two EV membrane proteins (B5 and A33) and to two MV membrane-associated proteins (L1 and A27) as a measure of virus replication. Animals passively immunized with VIG (5 mg) raised antibodies to all 4 proteins, indicating significant virus replication, which was consistent with the considerable weight loss of these animals. In contrast, antibodies to the VACV proteins were much lower in animals that received the highest amount of MAb (90 μg) and exhibited minimal weight loss. More intriguing were the results obtained with animals receiving 22.5 or 45 μg of MAb. These animals also did not make a response to either of the EV membrane proteins, but did make a dose-dependent response to the MV membrane-associated proteins. There are several possible explanations for this dichotomy. The simplest is that EV membrane proteins are less immunogenic than MV proteins and higher amounts of virus replication are needed for a response. However, the protection achieved with the low dose MAb and VIG was not statistically different. An alternative explanation for the difference in antibody response to EV-specific proteins is that the B5 MAb aggregated progeny EV on the infected cell surface and prevented the induction of antibodies to EV membrane proteins specifically. Indeed, agglutination of progeny EV on the surface of infected cells has been suggested as the mechanism by which EV antibodies prevent the formation of comet plaques (Law, M. & Smith, G. L. 2001 *Virology* 280: 132-142).

The use of anti-B5 MAbs in treatment of smallpox vaccine-associated complications would overcome the limitations posed by VIG, such as a low titer of neutralizing activity, variability and risk of transmission of infectious agents. It is especially important that anti-B5 MAbs cross-reacted with variola virus B5 and neutralized variola virus in vitro. Amino acid sequence comparison of B5 at residues 20 to 130 (a neutralization epitope recognized by the anti-B5 MAb) from vaccinia, variola and monkeypox viruses revealed that there are 10 amino acid differences between vaccinia and variola viruses, but only 4 amino acid differences between vaccinia and monkeypox viruses, and 3 of these are the same as in variola virus. Therefore, it is reasonable to assume that anti-B5 MAb would neutralize monkeypox virus also since it can neutralize variola virus. It is conceivable that an anti-B5 MAb alone or in conjunction with other MAbs could be used directly in treatment of bioterrorist-associated smallpox or in case of a monkeypox outbreak (Perkins, S. 2003 *Contemp Top Lab Anim Sci* 42:70-72).

Our anti-B5 MAb recognized a conformational epitope that is located between residues 20 and 130. Previously, two major neutralizing epitopes in B5 had been identified by testing a panel of 26 mouse anti-B5 MAbs; one epitope is localized to the SCR1-SCR2 border and the other is located in the stalk region (Aldaz-Carroll et al. 2005 *J Virol* 79:6260-6271). The neutralization epitope recognized by the chimpanzee/human MAb may be different from those previously reported (Aldaz-Carroll et al. 2005 *J Virol* 79:6260-6271). However, it is not possible to make a direct comparison because of the different mapping methods employed. Our method is based on differential binding of the MAb to a series of N- and C-terminally deleted peptides and the smallest peptide that still reacted strongly with the MAb was considered to be a binding site whereas the other method is based on differential binding of a MAb to a series of synthetic, linear overlapping peptides (Aldaz-Carroll et al. 2005 *J Virol* 79:6260-6271).

In summary, we have generated from the bone marrow of two immunized chimpanzees human-like MAbs that neutralize the extracellular form of VACV as well as that of variola virus. The MAbs protect mice from lethal challenge with virulent VACV and are therapeutic when administered two days after exposure. These MAbs provide the first alternative to VIG for treatment of complications of smallpox vaccination and a basis for the prevention and treatment of smallpox.

Chimpanzee Monoclonal Antibodies to Vaccinia Virus A33 Protein Protect Mice Against Vaccinia Virus and Neutralize Vaccinia and Smallpox Viruses Isolation and Characterization of Vaccinia A33-Specific Fabs The chimpanzee Fab-displaying phage library was panned against recombinant vaccinia virus (VACV) A33 protein and 96 individual clones were randomly picked and screened for binding to A33 by phage ELISA with BSA as a negative control. Ninety percent of the clones preferentially bound to A33. DNA sequencing of the variable regions of heavy (VH) and light (VL) chains from 16 positive clones showed that there were three distinct clones. These three clones were designated 6C, 12C, and 12F. The sequences of VH and VL genes are shown in FIGS. 6a and 6b. The closest human germline gene for each VH and VL gene was identified by searching V-Base database (Cook, G. P. & Tomlinson, I. M. 1995 *Immunol Today* 16:237-242) (Table 2).

TABLE 2

Human Ig Germ Line Genes Most Closely Related to Chimpanzee Heavy and Light Chains of Anti-A33 Mabs.

| MAb | VH Family | VH Segment | D Segment | JH Segment | $V_\lambda$ Family | $V_\lambda$ Segment | $J_\lambda$ Segment |
|---|---|---|---|---|---|---|---|
| 6C | VH7 | VI-4.1B | D3-10 | J5b | $V_\lambda$ I | 1b.366F5 | $J_\lambda$ 3b |
| 12C | VH1 | DP-25 | D3-10 | J4b | $V_\lambda$ III | 3r.9C5 | $J_\lambda$ 2/3a |
| 12F | VH5 | DP-73 | D3-3 | J5b | $V_\lambda$ II | 2a2.272A12 | $J_\lambda$ 2/3a |

The closest human VH and $V_\lambda$ germ line genes were identified by V-BASE database.

Figure 7:
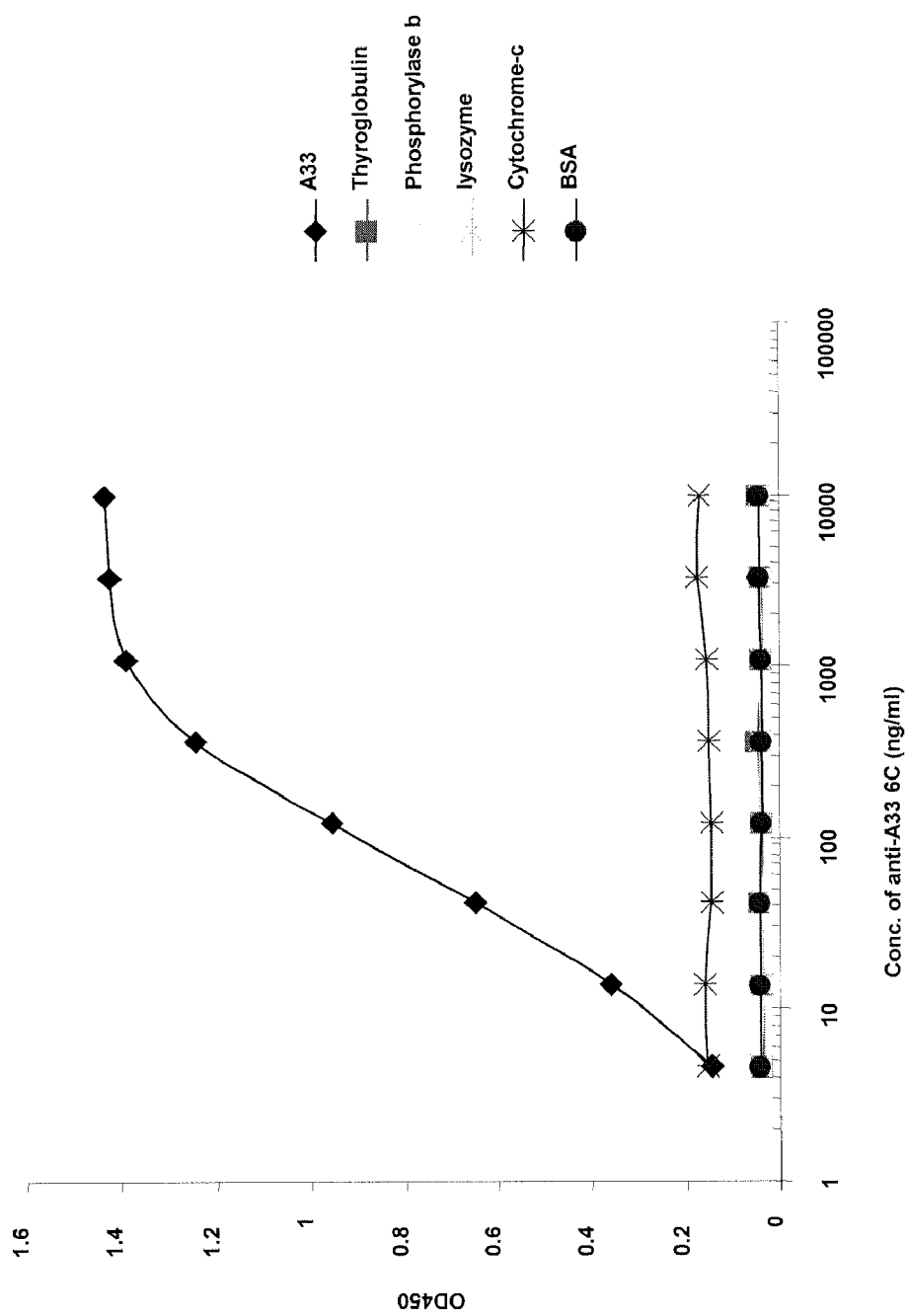
FIG. 7. Binding specificity of anti-A33 MAb 6C.

The Fab sequences were converted into full-length IgG with human γ1 constant regions and the IgGs were examined for their binding specificity by ELISA. Anti-A33 bound to A33 protein with high specificity, but not to unrelated proteins (BSA, thyroglobulin, phosphorylase b, lysozyme and cytochrome-c) (FIG. 7). The other two anti-A33 MAbs had the identical binding specificity.

Epitope Recognized by the Anti-A33 MAb

Figure 8:
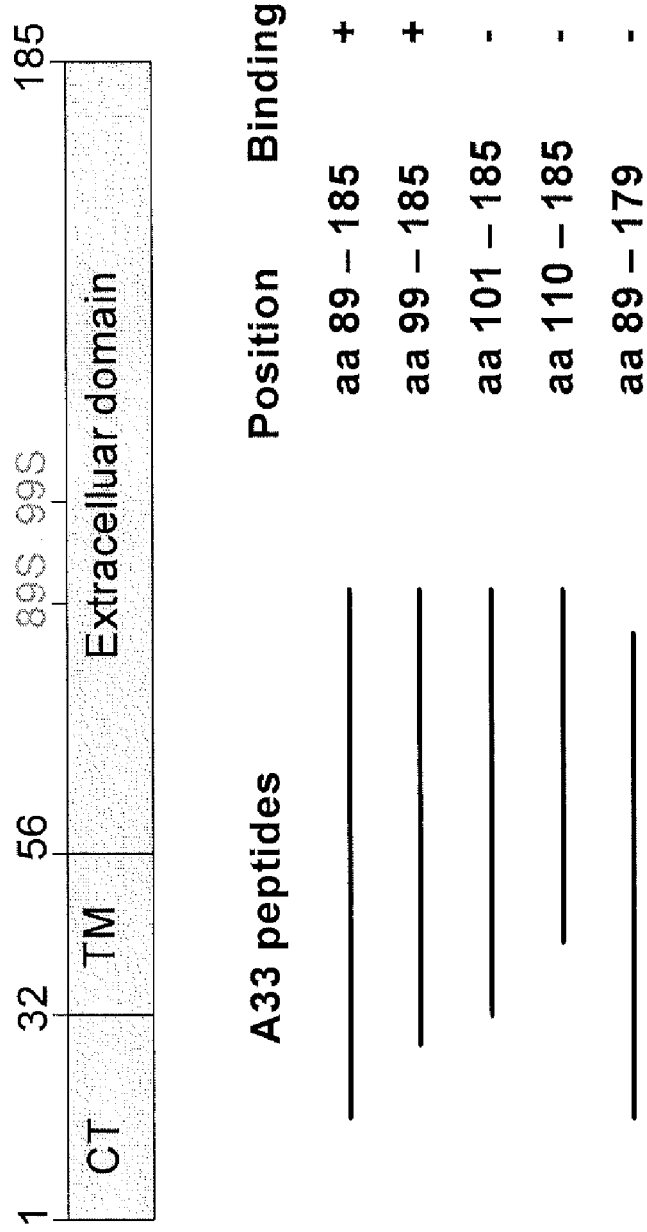
FIG. 8. Epitope mapping of anti-A33 MAb.
Figure 9A:
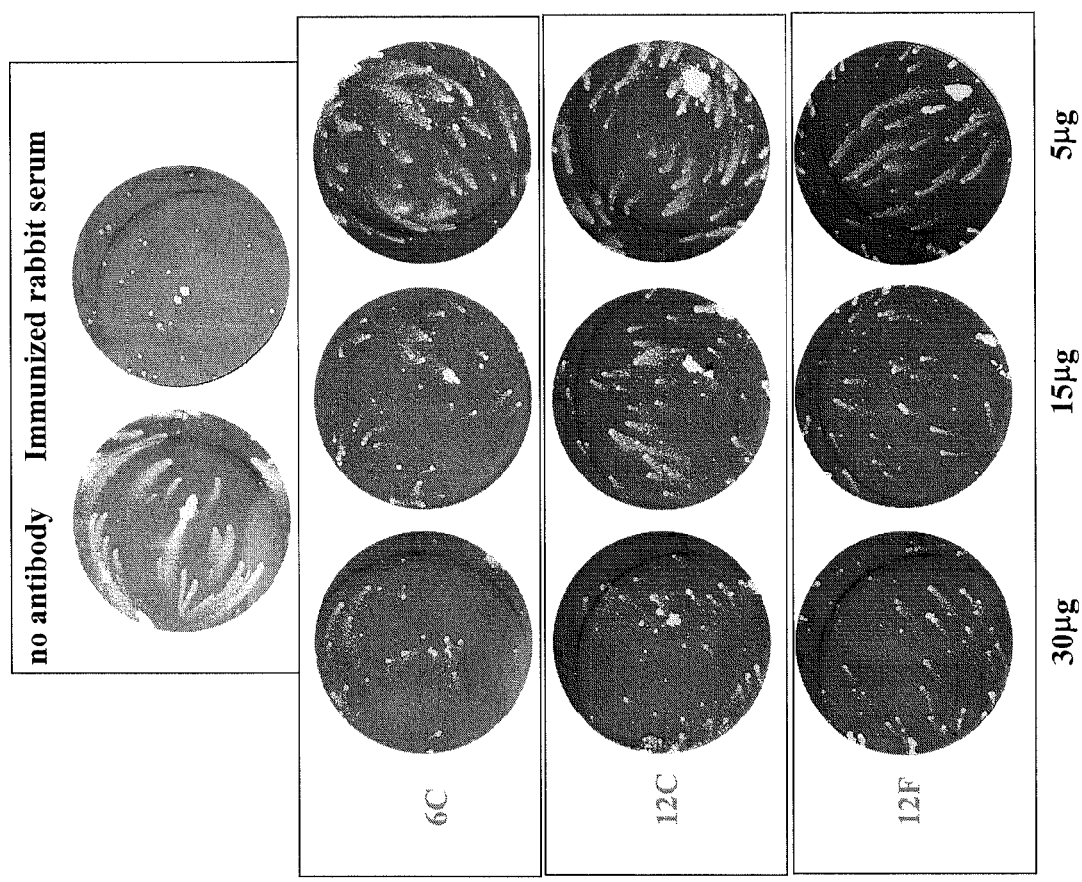
FIG. 9. Comet reduction assay for (a) vaccinia virus with anti-A33 MAbs and (b) variola virus with anti-A33 MAb 6C.
Figure 9B:
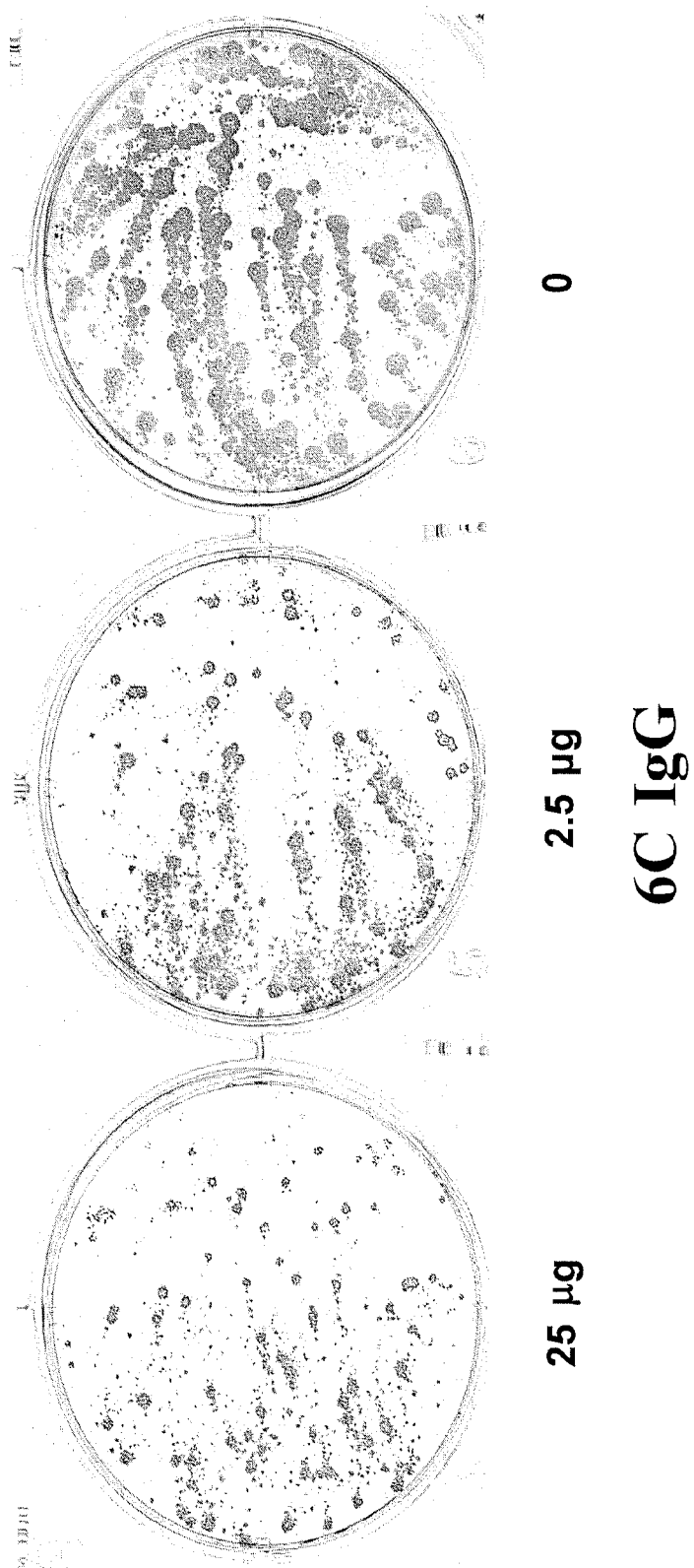
Figure 10:
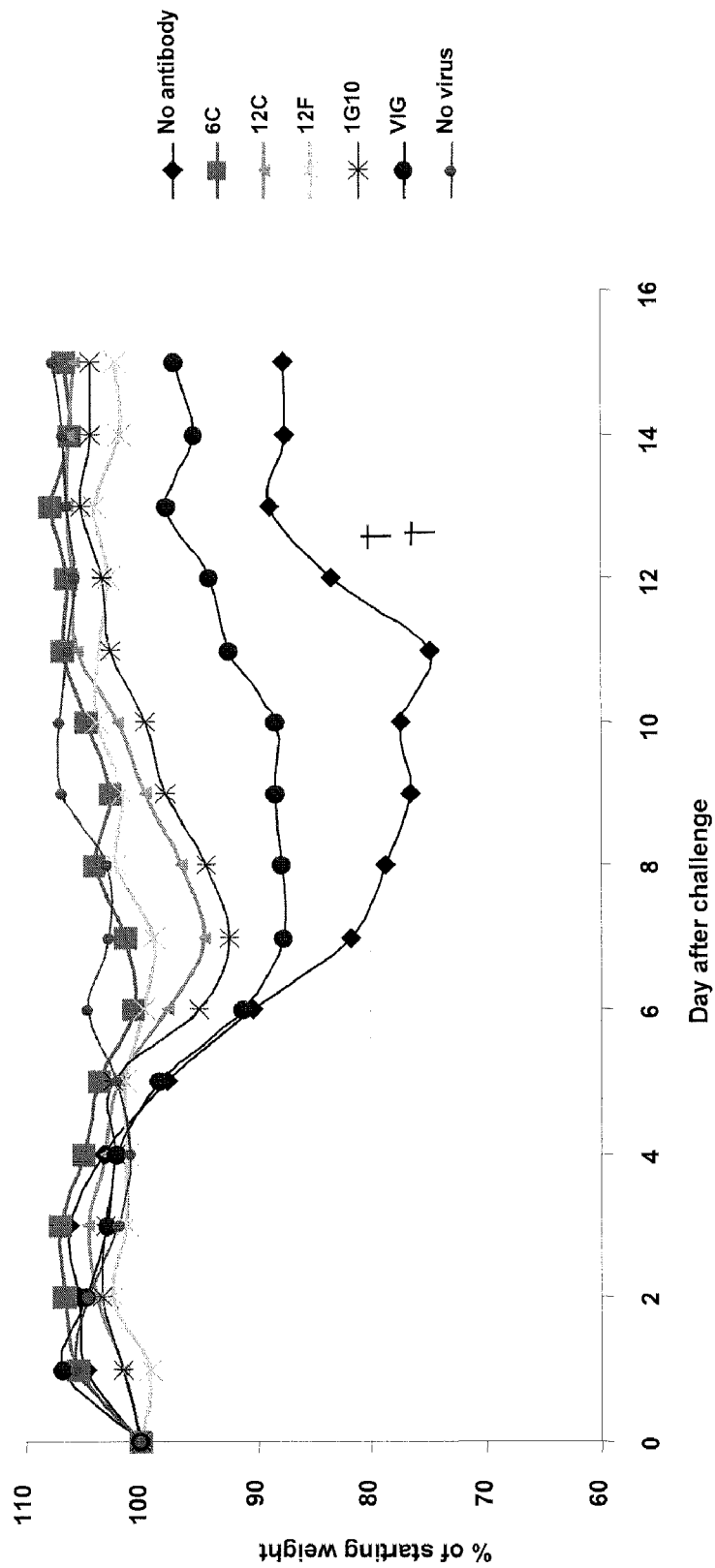
FIG. 10. In vivo neutralization of extracellular mature vaccinia virus by chimpanzee/human monoclonal anti-A33: Challenged with $10^5$ virulent vaccinia viruses.

Competition ELISA indicated that the three MAbs may recognize the same or closely related epitopes since they compete with each other for binding to A33 protein. Therefore, 6C was chosen for epitope mapping as it has been used for neutralization assay extensively. His-tagged soluble A33 peptides generated by N- and C-terminal deletions were produced in bacteria and affinity-purified through a nickel column. Western blotting with anti-His confirmed the identity of each peptide. However, the peptides did not react with anti-A33 MAb 6C in Western blots, which suggests that the epitope recognized by the anti-A33 MAb is conformational. To date, the shortest peptide that reacted strongly with MAb 6C in ELISA consisted of amino acids 99-185 (FIG. 8).

Binding Affinity and In Vitro Neutralizing Activity

The affinity of the three chimpanzee/human MAbs for binding A33 protein was measured by surface plasmon resonance (SPR) biosensor. $K_d$ range of 0.14 nM to 20 nM and a dissociation rate constant of $\sim 10^{-5}$/sec was observed for the three MAbs (Table 3).

TABLE 3

Binding affinities of anti-33 Mabs.

| MAb | $k_{on}$ ($M^{-1}s^{-1}$) | $k_{off}$ ($s^{-1}$) | $K_d$ |
|---|---|---|---|
| 6C | $6.8 \times 10^3$ | $1.35 \times 10^{-4}$ | 20 nM |
| 12C | $4.6 \times 10^4$ | $2.15 \times 10^{-5}$ | 0.46 nM |
| 12F | $1.85 \times 10^5$ | $2.58 \times 10^{-5}$ | 0.14 nM |

Since A33 is an EV-specific protein, in vitro neutralization activity of anti-B5 MAbs was measured by the comet-reduction assay, an established method that measures the inhibition of comet-like plaque formation by the released EV form of the virus (Appleyard, G. et al. 1971 *J Gen Virol* 13:9-17; Law, M. et al. 2002 *J Gen Virol* 83:209-222). The EV of the IHD strain of VACV formed comet-shaped plaques in the absence of antibodies, but the formation of comets was completely blocked by the addition of an excess of rabbit hyperimmune serum to VACV (FIG. 9*a*). The monoclonal anti-A33 clones, 6C, 12C and 12F, reduced the formation of comet-like plaques of vaccinia virus EV in a dose-dependent manner (FIG. 9*a*). Similarly, the formation of comet-shaped plaques of the Solaimen strain of variola EV was inhibited by 6C in a dose-dependent manner (FIG. 9*b*), indicating that the anti-A33 MAbs possessed neutralizing activity against EV of both viruses.

Protection of Mice Against Challenge with Virulent VACV

The BALB/c mouse pneumonia model of VACV challenge (Smee, D. F. et al. 2001 *Antiviral Res* 52:55-62; Williamson, J. D. et al. 1990 *J Gen Virol* 71:2761-2767) was used for the following reasons: weight loss and death are correlated with replication in the lungs, allowing the onset and progress of disease to be monitored by a non-invasive method that reduces the number of animals needed for significance (Law, M. et al. 2005 *J Gen Virol* 86:991-1000); the model has been used for active immunization studies with live VACV as well as with individual VACV proteins (Fogg, C. et al. 2004 *J Virol* 78:10230-10237) and for passive immunization studies with antisera prepared against VACV and VACV proteins (Law, M. et al. 2005 *J Gen Virol* 86:991-1000), and the intranasal (IN) route is believed to be the major avenue for transmission of variola virus. Groups of five BALB/c mice were inoculated intraperitoneally with 90 μg of purified IgG of chimpanzee/human MAbs 6C, 12C, 12F, or mouse MAb 1G10[8] or 5 mg of human vaccinia immune globulin (VIG). After 24 h, the mice were inoculated intranasally with $10^5$ pfu of vaccinia virus, strain WR. Mice were weighed individually and mean percentages of starting weight were plotted. Controls were unimmunized (no antibody) or unchallenged (no virus). Mice that died naturally or were killed because of 30% weight loss are indicated (†). The control mice lost weight continuously starting on day 5 following challenge and 2 of the 5 mice were sacrificed because they reached 70% of starting weight (FIG. 10). In contrast, the mice that were injected with MAbs 6C or 12F did not lose weight after the identical challenge, indicating that full protection was achieved. The mice receiving 12C experienced only slight weight loss, followed by rapid recovery. The mice receiving the mouse MAb 1G10 or human VIG were protected, but the protective efficacy was less than that afforded by the chimpanzee/human MAbs.

EXAMPLE 1

Reagents

Recombinant truncated B5 protein (275t) consisting of amino acids 20 to 275 was produced in a baculovirus expression system (Aldaz-Carroll et al. 2005 *J Virol* 79:6260-6271) and was used as a panning antigen for selection of B5-reactive phage. Restriction and other enzymes were from New England BioLab (Beverly, Mass.). Oligonucleotides were synthesized by Invitrogen (Carlsbad, Calif.). Anti-His horseradish peroxidase (HRP) conjugate, anti-human Fab HRP conjugate and anti-human Fab agarose were purchased from Sigma (St. Louis, Mo.). VACV WR (ATCC VR-1354), IHD-J (from S. Dales, Rockefeller University), and VV-NP-siinfekl-EGFP were grown in HeLaS3 cells (ATCC CCL-2.2), purified, and titered in BS-C-1 cells as described (Earl, P. L. et al. 1998 *Current Protocols in Molecular Biology* (Greene & Wiley, New York)). A rat anti-B5 MAb, from hybridoma 19C2 (Schmelz, M. et al. 1994 *J Virol* 68:130-147), was purified from ascitic fluid (Taconic Biotechnology, Germantown, N.Y.). VIG (Cangene) was obtained from the Centers for Disease Control (CDC) (C. Allen, Drug Service, Atlanta, Ga.).

Animals

Chimpanzees 3863 and 3915 were immunized twice approximately 19 years apart (initially at Bioqual, Inc, Rockville, Md. and subsequently at the University of Texas M.D. Anderson Cancer Center, Bastrop, Tex.) with VACV WR (Moss, B. et al. 1984 *Nature* 311:67-69). Bone marrow was aspirated from the iliac crests of these animals 11 weeks after the second immunization. Mice were purchased from Taconic Biotechnology (Germantown, N.Y.). All animal experiments were performed under protocols approved by the respective institutions as well as by the NIAID Animal Care and Use Committee.

Library Construction and Selection

Fab-encoding gene fragments were amplified from the cDNA of chimpanzee bone marrow-derived lymphocytes and cloned into pComb3H vector (Barbas, C. F. et al. 1991 *Proc Natl Acad Sci USA* 88:7978-7982; Schofield, D. J. et al. 2000 *J Virol* 74:5548-5555). The phage library was panned against B5 protein and specific phage clones were selected as described (Harrison, J. L. et al. 1996 *Methods Enzymol* 267: 83-109). The details of library construction and selection are provided in Example 2.

Sequence Analysis

The genes encoding the variable region of the heavy (VH) and light (VL) chains of B5-specific clones were sequenced, and their corresponding amino acid sequences were aligned. The presumed family usage and germline origin were established for each VH and VL gene by search of V-Base (Cook, G. P. & Tomlinson, I. M. 1995 *Immunol Today* 16:237-242).

Expression and Purification of Fab and IgG

The phagemid containing λ light chain and γ1 heavy chain was cleaved with NheI and SpeI and recircularized following removal of the phage gene III DNA fragment from the vector in order to encode soluble Fab. Bacteria containing circularized DNA without phage gene III were cultured in 2× YT medium containing 2% glucose, 100 μg/ml ampicillin and 15 μg/ml tetracycline at 30° C. until the $OD_{600}$ reached 0.5-1. The culture was diluted 5-fold in 2× YT medium without glucose and containing 0.2 mM isopropyl β-D-thiogalactoside (IPTG) and culture was continued at 27° C. for 20 h for expression of soluble Fab. Since the Fab was tagged at the C-terminus with $(His)_6$, the expressed proteins were readily affinity-purified on a nickel-charged column.

The conversion of Fab to full-length IgG was achieved by digestion of γ1 Fd with XhoI and ApaI and cloning it into pCDHC68B vector (Trill, J. J. et al. 1995 *Curr Opin Biotechnol* 6:553-560), which contains the human heavy chain constant region; the λ-chain was cloned into pCNHLCVector3 (Trill, J. J. et al. 1995 *Curr Opin Biotechnol* 6:553-560) at XbaI and SacI sites. For full-length IgG expression and purification, plasmids containing heavy chain and light chain were co-transfected into 293T cells for transient expression. The IgG was purified by affinity chromatography with anti-human Fc agarose (Sigma).

The purity of the Fab and IgG was determined by SDS-PAGE and the protein concentration was determined by BCA assay (Pierce, Rockford, Ill.) and spectrophotometer measurement at $OD_{280}$.

ELISA Assay

B5 (275t) and non-related proteins (BSA, cytochrome-c, thyroglobulin, lysozyme, phosphorylase b) were coated in a 96-well plate by placing 100 μl containing 1-5 μg/ml protein in 1× PBS, pH7.4 in each well and incubating the plate at room temperature (RT) overnight. Serial dilutions of soluble Fab, IgG or phage were added to the wells and plates were incubated for 2 h at RT. The plates were washed and the secondary antibody conjugate (anti-His-HRP, anti-human Fab-HRP, or anti-M13-HRP) was added and incubated for 1 h at RT. The plates were washed and the color was developed by adding TMB (Sigma). The plates were read at OD450 in an ELISA plate reader.

Affinity Measurement

SPR biosensing experiments were conducted with a Biacore 3000 instrument (Biacore, Piscataway, N.J.) using short carboxy-methylated dextran sensor surfaces (CM3, Biacore) and standard amine coupling as described in detail elsewhere (Schuck, P. et al. 1999 in *Current Protocols in Protein Science* (John Wiley & Son, New York)). The procedure is described in Example 3.

Epitope Mapping

The epitope recognized by anti-B5 8AH8AL was mapped by Western blot. B5 peptides corresponding to aa 20-275, 20-160, 20-130, 20-100, 33-275, 56-275, 71-275 were synthesized in *E. coli* as described previously (Zhou, Y. H. et al. 2004 *Vaccine* 22:2578-2585). The analysis is described in Example 4.

Comet Reduction Assay for VACV

Monolayers of BS-C-1 cells in 6-well cell culture plates were infected with the IHD-J strain of VACV, which releases more EV than the WR strain, at 50 to 100 plaque-forming units per well in Minimal Essential Medium containing 2.5% FBS (MEM-2.5). After incubation for 2 h at 37° C., the medium was aspirated; cells were washed twice, and overlaid with MEM-2.5 containing the antibodies to be tested. The plates were then placed in a CO2 incubator for 36 h. Comets were visualized by staining the monolayers with a solution of 0.1% crystal violet in 20% ethanol. Each MAb was tested at several concentrations (5-30 μg per well). Rabbit polyclonal hyperimmune serum was used as a positive control.

Comet Reduction Assay for Variola Virus

The experiment was carried out in a BSL-4 smallpox laboratory at the CDC. Monolayers of BS-C-40 cells in 6-well cell culture plates were infected with the Solaimen strain of variola virus at 50 plaque-forming units per well in RPMI medium containing 2% FBS. After 1 h, the medium was aspirated; cells were washed twice, and overlaid with RPMI containing antibody at different concentrations. Each treatment was duplicated. The plates were then incubated at a fixed angle in a $CO_2$ incubator for 4 days at 35.5° C. Cells were fixed and reacted with polyclonal rabbit anti-variola antibody (Yang, H. et al. 2005 *J Clin Invest* 115:379-387). Following incubation with goat anti-rabbit-HRP conjugate, comets were visualized by addition of TruBlue peroxidase substrate (KPL).

Passive Immunization and Challenge with VACV Strain WR

Groups of seven-week old female BALB/c mice (Taconic Biotechnology, Germantown, N.Y.) were inoculated intraperitoneally with antibody diluted in PBS. Non-immunized controls were injected with the same volume of PBS. Either 24 h after or 48 h before immunization, mice were challenged intranasally with $10^5$ plaque forming units (PFU) of VACV WR as described (Fogg, C. et al. 2004 *J Virol* 78:10230-10237). Mice were weighed daily for 16 days and sacrificed if their weight diminished to 70% of the initial weight, in accordance with NIAID Animal Care and Use protocols. Mice were bled 24 h after passive immunization to monitor administered antibody levels and on day 22 to measure development of antibodies to the challenge virus.

Evaluation of Murine Convalescent Antibody Response Following Challenge

Serum samples taken from mice 22 days after challenge with VACV (see above) were analyzed for induction of mouse antibodies to recombinant proteins B5, A33, L1 (Aldaz-Carroll, L. et al. 2005 *Virology* 341:59-71), and A27 and neutralizing antibodies against MV. The recombinant proteins were used to coat 96-well plates as described (Fogg, C. et al. 2004 *J Virol* 78:10230-10237) and two-fold serial dilutions of sera were added to the plates. The bound mouse antibodies were detected by anti-mouse IgG(γ)-peroxidase (Roche, Indianapolis, Ind.). The substrate 3,3',5,5'-tetramethylbenzidine (BM Blue, POD, Roche) was used and endpoint titers were calculated as the dilution with absorbance ($A_{370}$ and $A_{492}$) values two standard deviations above that measured in wells without antibodies. The $IC_{50}$ values for neutralization of the MV form of VACV were determined by flow cytometry using the reporter virus VV-NP-siinfekl-EGFP as described (Earl, P. L. et al. 2003 *J Virol* 77:10684-10688).

Statistical Analysis

Statistical differences in weight loss between groups of mice were assessed by analysis of variance (ANOVA) using StatView software (SAS Institute, Inc., Cary, N.C.).

EXAMPLE 2

Bone marrow-derived lymphocytes were isolated by Ficoll gradient separation. Messenger RNA was extracted from $10^8$ lymphocytes with an mRNA purification kit (Amersham Biosciences, Piscataway, N.J.). The 1st strand cDNA was synthesized from mRNA with a first-strand cDNA synthesis kit from Amersham Biosciences. The γ1 heavy chain Fd cDNA was amplified by polymerase chain reaction (PCR) using nine human γ1 heavy chain-specific 5' primers in combination with a chimpanzee γ1-specific 3' primer. The λ chain cDNA was amplified by PCR with seven human λ chain-specific 5' primers and a 3' primer matching the end of the constant region (Barbas, C. F. et al. 1991 *Proc Natl Acad Sci USA* 88:7978-7982; Schofield, D. J. et al. 2000 *J Virol* 74:5548-

5555). PCR was performed for 30 cycles at 95° C., 1 min, 52° C., 1 min, and 72° C., 1 min with AmpliTaq DNA polymerase (Applied Biosystems, Foster City, Calif.). Chimpanzee λ light chain and γ1 heavy chain DNA fragments were cloned into the pComb3H phagemid as described previously (Barbas, C. F. et al. 1991 *Proc Natl Acad Sci USA* 88:7978-7982; Schofield, D. J. et al. 2000 *J Virol* 74:5548-5555). Briefly, amplified λ chain DNA fragments were pooled, purified, digested with SacI and XbaI and cloned into pComb3H at the SacI and XbaI sites. The recombinant plasmid DNA was introduced into *Esherichia coli* Top 10 (Invitrogen) by electroporation, yielding $1 \times 10^7$ individual clones. The plasmid DNA containing λ light chain sequences was digested with XhoI and SpeI, and γ1 heavy chain DNA cut with the same enzymes was inserted. The plasmid DNA containing both light and heavy chains was transformed into *E. coli* Top10 by electroporation, resulting in a Fab-displaying library with $5 \times 10^7$ individual clones.

The phagemid was rescued by superinfection with helper phage, VCS-M13 (Stratagene, La Jolla, Calif.) and phagemids carrying Fab on their tips were subjected to panning on B5 (275t) protein coated on ELISA wells. Nonspecifically adsorbed phages were removed by extensive washing. Specifically bound phages were eluted with 100 mM triethylamine, neutralized to pH 7.5, amplified and used for further selection as described (Harrison, J. L. et al. 1996 *Methods Enzymol* 267:83-109). After three rounds of panning, randomly picked single Fab-bearing phage clones were screened for specific binding to B5 (275t) by ELISA. Briefly, 96-well ELISA plates were coated with 0.1 µg of B5 (275t) or control protein BSA and blocked with PBS containing 3% nonfat milk. Fab-bearing phages in PBS containing 3% nonfat milk were added. Specifically bound phages were detected by adding HRP-conjugated mouse anti-M13, and the color was developed by adding tetramethylbenzidine (TMB) substrate. Absorbance at 450 nm was measured after adding sulphuric acid. Clones that differentially bound to B5 with A450 values of >1.0 were scored as positive, whereas values of <0.2 were scored as negative.

EXAMPLE 3

Affinity Measurement

Surfaces were activated with N-hydroxysuccinimide and N-ethyl-N'-(3-dimethylaminopropyl)carbodiimide hydrochloride, reacted with antibody solutions at low ionic strength at pH 5.0, and unreacted groups were quenched with ethanolamine. Binding experiments were conducted at a flow rate of 5 µl/min in 10 mM HEPES, 150 mM NaCl, 3 mM EDTA, 0.005% v/v surfactant P20 at pH 7.4 and 25° C., and the surface was regenerated with 10 mM glycine-HCl pH 2.0.

Anti-B5 IgG was immobilized to the surface and the kinetics of binding and dissociation of B5 (275t) was recorded for 50 min and 3 h, respectively, at B5 (275t) concentrations between 0.05 and 500 nM. In order to eliminate the effect of immobilization-induced surface site heterogeneity in the determination of the binding constants (Schuck, P. 1997 *Annu Rev Biophys Biomol Struct* 26:541-566), the kinetic traces were globally fitted with a model for continuous ligand distributions (Svitel, J. et al. 2003 *Biophys J* 84:4062-4077). This resulted in residuals of the global fit that were evenly distributed and of a magnitude in the order of noise of the data acquisition (root-mean-square deviation below 0.5 RU). No terms for mass transport limitation were necessary. Since the 8AH8AL exhibited very slow kinetics, long extrapolation is required to determine the equilibrium constants from the kinetic assay. Therefore, as a control, a solution competition experiment was conducted, where soluble IgG at different concentrations was pre-incubated with B5 for 24 h, and the concentration of unbound B5 was determined from the initial slope of the surface binding when passing the mixture over the anti-B5 functionalized surface. The standard competition isotherm model was used for the analysis (Schuck, P. 1997 *Annu Rev Biophys Biomol Struct* 26:541-566; Schuck, P. et al. 1999 in *Current Protocols in Protein Science* (John Wiley & Son, New York)).

EXAMPLE 4

Epitope Mapping

The epitope recognized by anti-B5 8AH8AL was mapped by Western blot. B5 peptides corresponding to aa 20-275, 20-160, 20-130, 20-100, 33-275, 56-275, and 71-275 were synthesized in *E. coli* as described previously (Zhou, Y. H. et al. 2004 *Vaccine* 22:2578-2585). In brief, B5R DNA fragments encoding the above peptides were amplified from B5R cDNA (Isaacs, S. N. et al. 1992 *J Virol* 66:7217-7224) with primers containing PstI and HindIII sites at 5'- and 3'-ends, respectively, by PCR. PCR products were inserted into pRE-SET vector (Invitrogen) at PstI and HindIII sites. The sequence encoding a six-histidine tag in the vector was in frame with the insert DNA for easy detection and purification. The recombinant plasmid DNA carrying the B5R DNA insert was transformed into *E. coli* JM109 and the sequence of the insert was confirmed.

The recombinant plasmid DNA was subsequently transformed into *E. coli* BL21(DE3)pLysS (Invitrogen) for expression. In brief, the bacteria were cultured at 37° C. in SOB medium containing ampicillin and chloramphenicol and the expression was induced by IPTG. The bacteria were collected and resuspended in SDS-PAGE sample buffer. The amount of B5 peptides was estimated by SDS-PAGE (16% Tris-Glycine gel, Invitrogen) and Western blotting with HRP-conjugated anti-His. Approximately equal amounts of protein were separated by SDS-PAGE, transferred to nitrocellulose membrane, and probed with anti-B5 8AH8AL. The bound MAb on the membrane was detected by HRP-conjugated anti-human IgG F(ab')2 (Sigma). Following reaction with LumiGLO chemiluminescent peroxidase substrate (KPL, Gaithersburg, Md.), the positive bands were detected by exposing the membrane to X-ray film.

EXAMPLE 5

Truncated Smallpox B5 Constructed from Vaccinia Counterpart

To construct a truncated B5 protein with the smallpox virus sequence, eight primers containing all of the 10 amino acids that are specific for smallpox B5 were designed as follows:

```
B5-20F
                                    (SEQ ID NO: 81)
5'-AACTGCAGACATGTACTGTACCCACTATG-3'

MT-1F
                                    (SEQ ID NO: 82)
5'-TGATTCGGGATATTATTCTTTGGATCC-3'

MT-2R
                                    (SEQ ID NO: 83)
5'-GGATCCAAAGAATAATATCCCGAATCA-3'

MT-3F
                                    (SEQ ID NO: 84)
5'-ACAGTTTCTGATTACGTCTCTGAA-3'
```

```
MT-4R
                                                         (SEQ ID NO: 85)
5'-TTCAGAGACGTAATCAGAAACTGT-3'

MT-5F
                                                         (SEQ ID NO: 86)
5'-AATGCCATCATCACACTAATTTGCAAGGACGAA-3'

MT-6R
                                                         (SEQ ID NO: 87)
5'-TTCGTCCTTGCAAATTAGTGTGATGATGGCATT-3'

B5-130R
                                                         (SEQ ID NO: 88)
5'-AAAAGCTTACATTCCGCATTAGGACACGT-3'
```

Thirty cycles of PCR (94° C. for 25 seconds, 50° C. for 15 seconds, and 72° C. for 20 seconds) with primer pairs of B5-20F/MT-2R, MT-1F/MT-4R, MT-3F/MT-6R, and MT-5F/B5-130R generated 4 PCR products. The DNA fragment encoding amino acid residues 20-130 of smallpox B5 was created by overlapping extension PCR of the 4 PCR products. Briefly, equal amounts of the gel-purified PCR products were mixed with two flanking primers, B5-20F and B5-130R, and the mixture was amplified for 30 cycles (94° C. for 25 seconds, 55° C. for 15 seconds, and 72° C. for 1 min). The full-length PCR product was purified and cloned into pRESET vector and the DNA sequence of the insert was confirmed. The methods for protein expression and Western blotting analysis have been described in the epitope mapping section.

EXAMPLE 6

Figure 11:
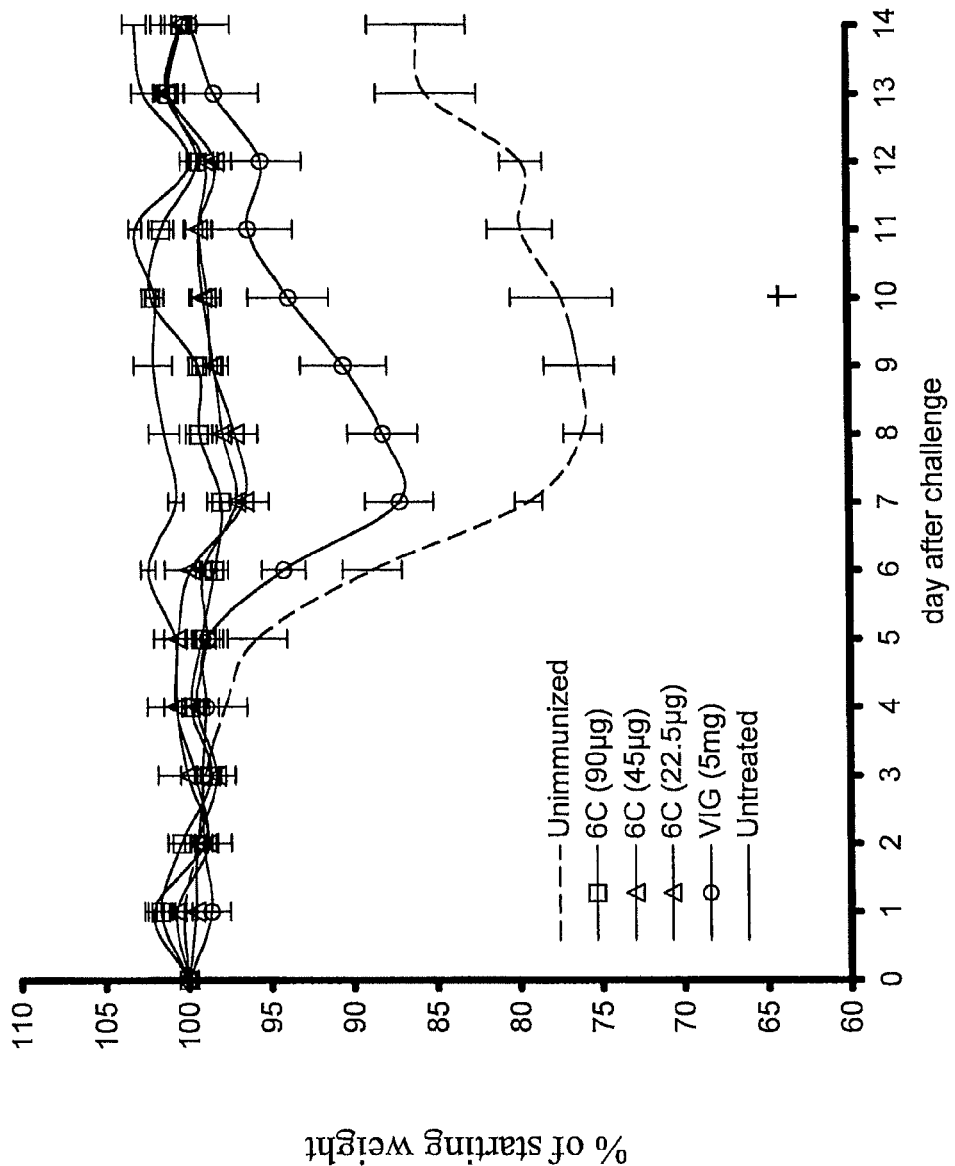
FIG. 11. Passive immunization of mice with chimpanzee/human monoclonal antibody 6C. Groups of seven-week old female BALB/c mice (Taconic Biotechnology, Germantown, N.Y.) were immunized with different amounts of monoclonal antibody 6C (90, 45, or 22.5 µg) or with 5 mg of vaccinia immune globulin (VIG) (Cangene). Antibodies were diluted in PBS and injected by the intraperitoneal route. Twenty four hours later, the animals were challenged intranasally with $10^5$ PFU of vaccinia virus WR. Mice were weighed daily for 14 days and were sacrificed if their weight diminished to 70% of the initial weight, in accordance with NIAID Animal Care and Use protocols.

To determine the minimum effective dose of anti-A33 6C, groups of mice (5 mice per group) were given decreasing amounts of 6C (90, 45, 22.5 µg per mouse) or a single 5 mg dose of human VIG (2.5× the recommended human dose on a weight basis). Twenty four hours later, the animals were challenged intranasally with $10^5$ PFU of VACA WR. Mice were weighed daily and the weight loss was used to estimate the protective efficacy. As shown in FIG. 11, mice receiving either mAb 6C or VIG had statistically significant less weight loss than the unimmunized mice (P<0.0001 at day 8). Better protection was achieved by mAb 6C than by VIG since almost no weight loss was observed for the mice given mAb 6C even at the lowest amount tested (22.5 µg), whereas the mice given VIG lost substantial weight. The difference in weight loss between mice given mAb 6C at all different doses and mice given VIG was statistically significant on day 8 (P<0.0001).

Figure 12:
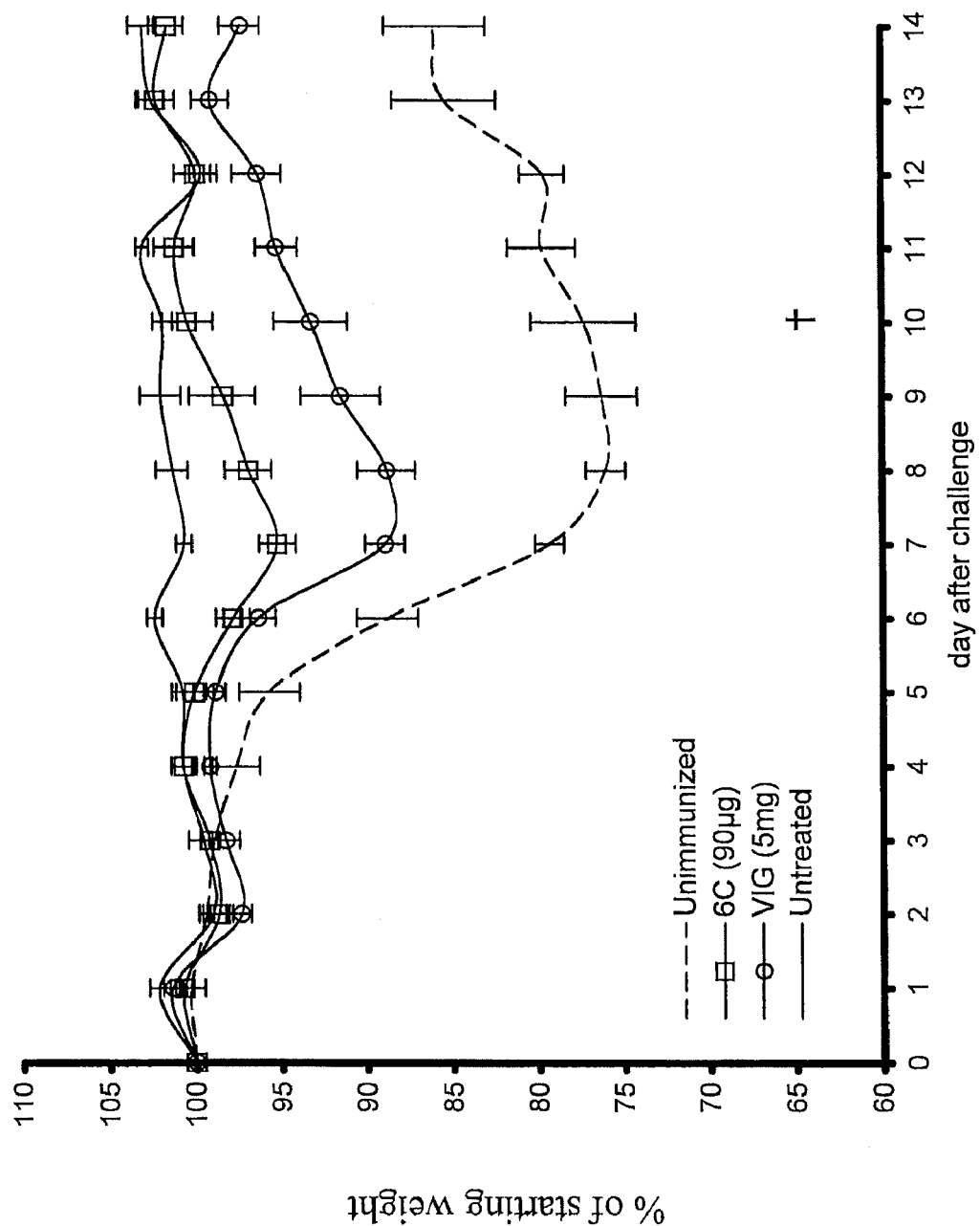
FIG. 12. Post-exposure treatment of mice with chimpanzee/human monoclonal antibody 6C. Groups of seven-week old female BALB/c mice (Taconic Biotechnology, Germantown, N.Y.) were challenged intranasally with $10^5$ PFU of vaccinia virus WR. Forty eight hours later, either 6C (90 µg) or VIG (5 mg) was administered by the intraperitoneal route. Mice were weighed daily for 14 days and were sacrificed if their weight diminished to 70% of the initial weight, in accordance with NIAID Animal Care and Use protocols.

To assess the therapeutic value of mAb 6C, the mAb or human VIG was administered to mice 2 days after challenge with VACA WR (FIG. 12). Mice given 6C had much less weight loss than those given VIG and the difference was statistically significant (P=0.002, on day 9). Nevertheless, both 6C and VIG provided significant protection as measured by weight loss (P<0.0001 on day 8, 6C-treated or VIG-treated versus untreated).

Figure 13:
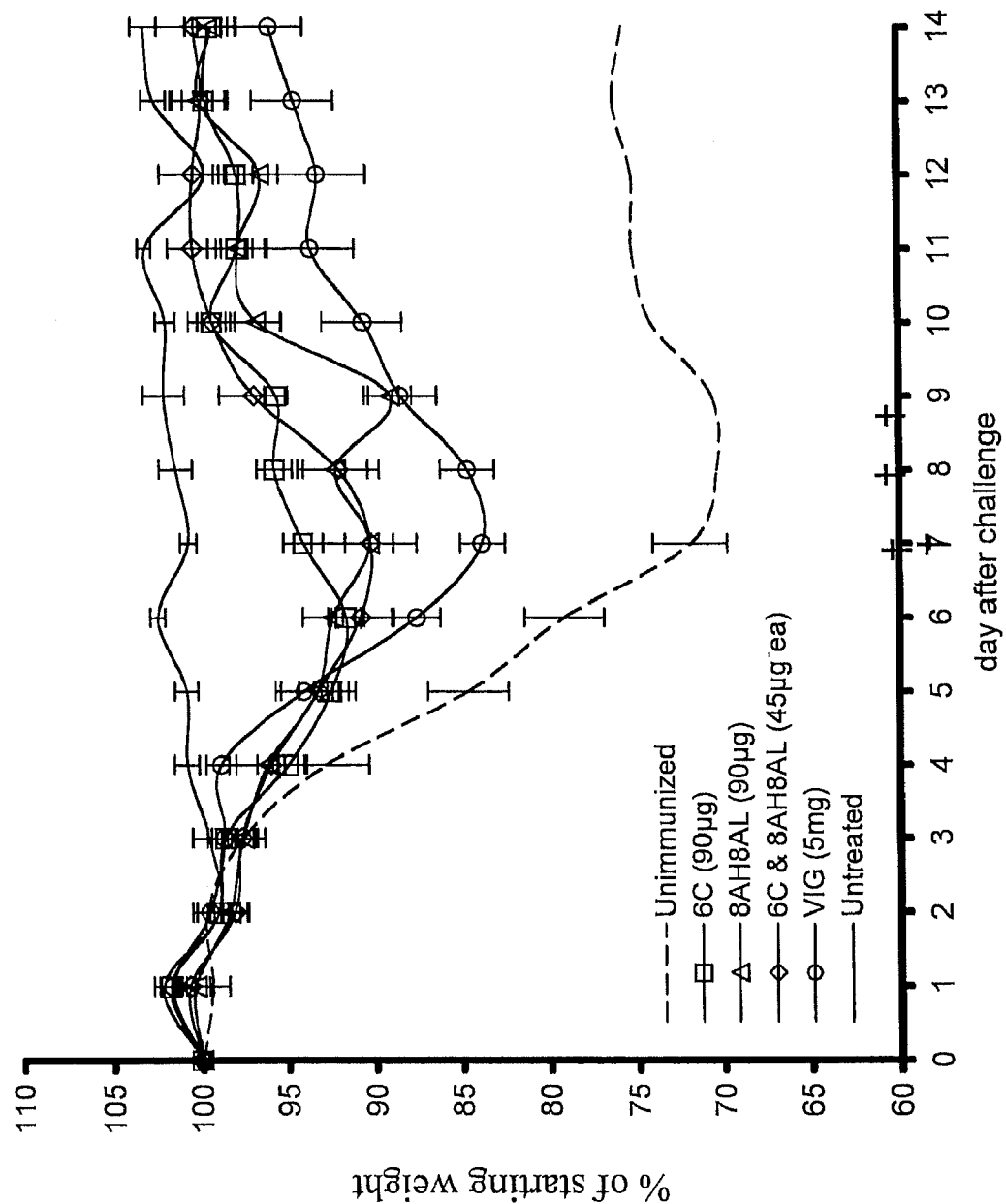
FIG. 13. Passive immunization of mice with chimpanzee/human monoclonal antibodies 6C and/or 8AH8AL. Groups of seven-week old female BALB/c mice (Taconic Biotechnology, Germantown, N.Y.) were immunized by the intraperitoneal route with 90 µg of 6C, 90 µg of 8AH8AL, 45 µg each of these antibodies, or 5 mg of VIG. Twenty four hours later, mice were challenged intranasally with $5 \times 10^5$ PFU of vaccinia virus WR. Mice were weighed daily for 14 days and were sacrificed if their weight diminished to 70% of the initial weight, in accordance with NIAID Animal Care and Use protocols.
Figure 14:
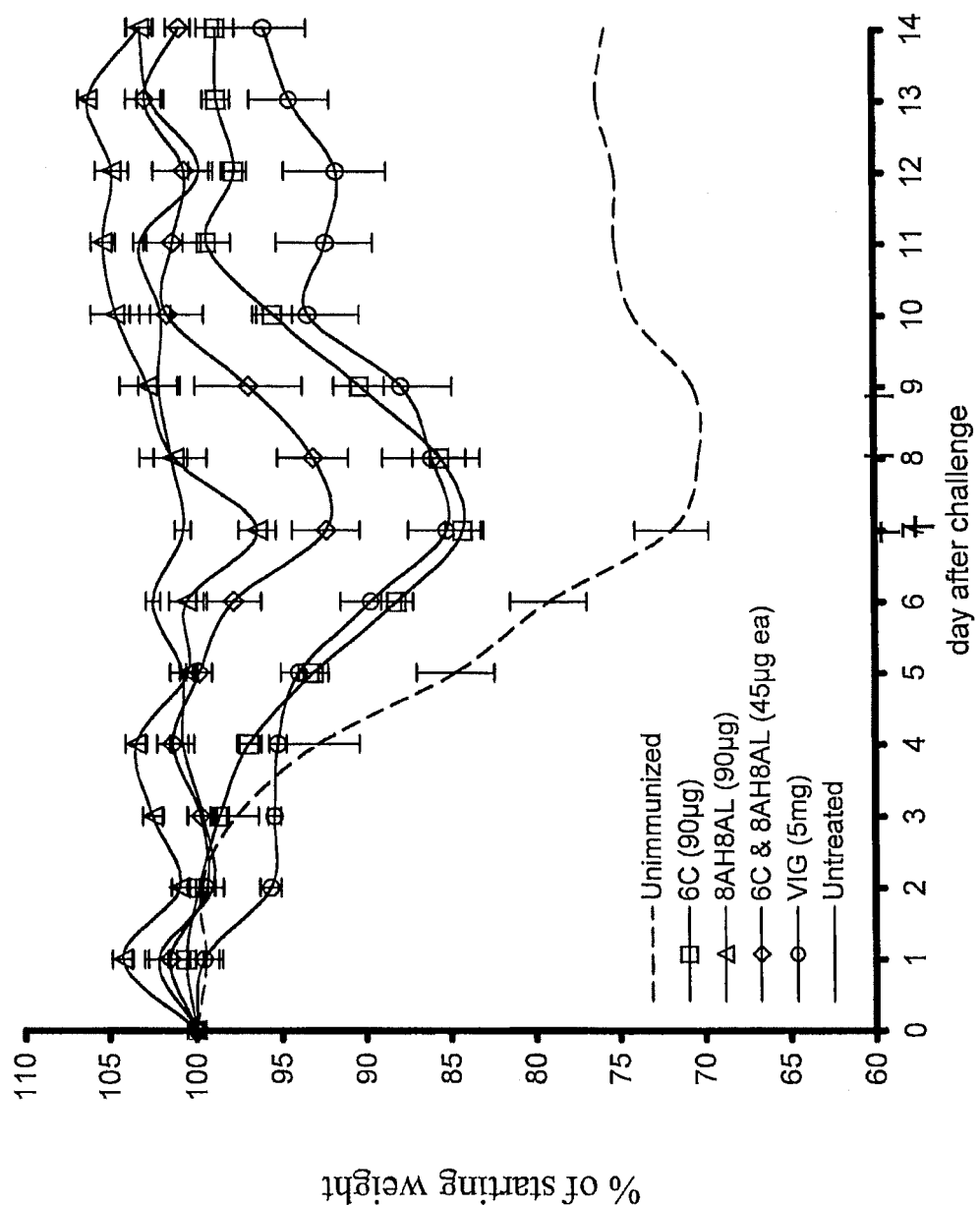
FIG. 14. Post-exposure treatment of mice with chimpanzee/human monoclonal antibodies 6C and/or 8AH8AL. Groups of seven-week old female BALB/c mice (Taconic Biotechnology, Germantown, N.Y.) were challenged intranasally with $5 \times 10^5$ PFU of vaccinia virus WR. Forty eight hours later either 90 µg of 6C, 90 µg of 8AH8AL, 45 µg each of these antibodies, or 5 mg of VIG was administered by the intraperitoneal route. Mice were weighed daily for 14 days and were sacrificed if their weight diminished to 70% of the initial weight, in accordance with NIAID Animal Care and Use protocols.

To determine if there was a synergistic effect between anti-B5 mAb 8AH8AL and anti-A33 6C, we compared the protective efficacy of the individual mAbs and VIG with that of a combination of the two mAbs in mice challenged with WR before and after administration of antibody (FIG. 13 and FIG. 14). The protective efficacy of two mAbs was not greater than that of the individual mAbs. mAb 6C appeared to protect slightly better than mAb 8AH8AL (P=0.0189 on day 10) when administered before challenge, whereas, 8AH8AL provided much stronger protection than 6C when administered after challenge (P<0.0001 on day 8).

EXAMPLE 7

Figure 15C:
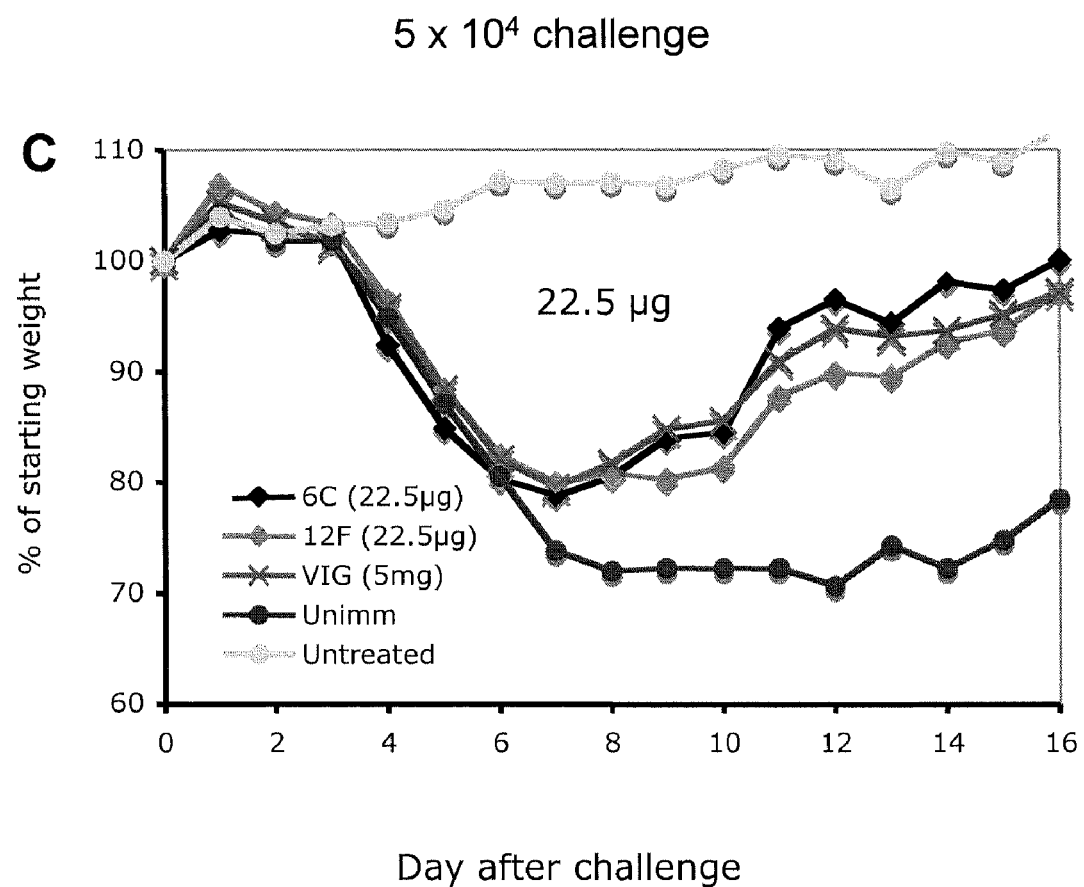
FIG. 15. Passive immunization of mice with chimpanzee/human monoclonal antibodies 6C or 12F. Groups of seven-week old female BALB/c mice (Taconic Biotechnology, Germantown, N.Y.) were immunized by the intraperitoneal route with either 90 µg, 45 µg, or 22.5 µg of antibody 6C or 12F, or with 5 mg of VIG. Twenty four hours later, mice were challenged intranasally with $5 \times 10^4$ PFU of vaccinia virus WR. Mice were weighed daily for 16 days and were sacrificed if their weight diminished to 70% of the initial weight, in accordance with NIAID Animal Care and Use protocols.

Anti-A33 MAb 12F had about 140-fold higher affinity than MAb 6C (Table 3). To determine if affinity was related to the protective efficacy of the antibodies, MAb 12F and MAb 6C were tested in parallel in the mouse pneumonia model at different doses. As shown in FIG. 15, the protection provided by 12F was no different from that provided by 6C. The possible reason for this result may be the dimeric nature of A33 protein, which makes antibody avidity, rather than affinity the dominant binding force.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. A substantially pure polypeptide comprising a fully human or humanized chimpanzee monoclonal antibody that binds A33 antigen, wherein said monoclonal antibody comprises:
   (a) heavy chain CDR1 region having the amino acid sequence of SEQ ID NO:35, a heavy chain CDR2 region having the amino acid sequence of SEQ ID NO:37, a heavy chain CDR3 region having the amino acid sequence of SEQ ID NO:39, a light chain CDR1 region having the amino acid sequence of SEQ ID NO:43, a light chain CDR2 region having the amino acid sequence of SEQ ID NO:45 and a light chain CDR3 region having the amino acid sequence of SEQ ID NO:47; or
   (b) heavy chain CDR1 region having the amino acid sequence of SEQ ID NO:51, a heavy chain CDR2 region having the amino acid sequence of SEQ ID NO:53, a heavy chain CDR3 region having the amino acid sequence of SEQ ID NO:55, a light chain CDR1 region having the amino acid sequence of SEQ ID NO:59, a light chain CDR2 region having the amino acid sequence of SEQ ID NO:61 and a light chain CDR3 region having the amino acid sequence of SEQ ID NO:63.

2. The substantially pure polypeptide of claim 1 wherein said antibody comprises a Fd fragment.

3. The substantially pure polypeptide of claim 1 wherein said antibody comprises a Fab fragment.

4. An anti-vaccinia virus A33 6C deposited with ATCC as ATCC Accession No. PTA-7323.

5. A pharmaceutical preparation comprising the monoclonal antibody of claim 1.

6. A diagnostic preparation comprising the monoclonal antibody of claim 1.

7. The substantially pure polypeptide of claim 1, wherein said monoclonal antibody comprises a heavy chain CDR1 region having the amino acid sequence of SEQ ID NO:35, a heavy chain CDR2 region having the amino acid sequence of SEQ ID NO:37, a heavy chain CDR3 region having the amino acid sequence of SEQ ID NO:39, a light chain CDR1 region having the amino acid sequence of SEQ ID NO:43, a light chain CDR2 region having the amino acid sequence of SEQ ID NO:45 and a light chain CDR3 region having the amino acid sequence of SEQ ID NO:47.

8. The substantially pure polypeptide of claim 7, wherein said monoclonal antibody comprises a $V_H$ region having the amino acid sequence of SEQ ID NO:33.

9. The substantially pure polypeptide of claim 7, wherein said monoclonal antibody comprises a $V_L$ region having the amino acid sequence of SEQ ID NO:41.

10. The substantially pure polypeptide of claim 1, wherein said monoclonal antibody comprises a heavy chain CDR1 region having the amino acid sequence of SEQ ID NO:51, a heavy chain CDR2 region having the amino acid sequence of SEQ ID NO:53, a heavy chain CDR3 region having the amino acid sequence of SEQ ID NO:55, a light chain CDR1 region having the amino acid sequence of SEQ ID NO:59, a light chain CDR2 region having the amino acid sequence of SEQ ID NO:61 and a light chain CDR3 region having the amino acid sequence of SEQ ID NO:63.

11. The substantially pure polypeptide of claim 10, wherein said monoclonal antibody comprises a $V_H$ region having the amino acid sequence of SEQ ID NO:49.

12. The substantially pure polypeptide of claim 10, wherein said monoclonal antibody comprises a $V_L$ region having the amino acid sequence of SEQ ID NO:57.

13. The pharmaceutical preparation of claim 5, wherein said monoclonal antibody comprises a heavy chain CDR1 region having the amino acid sequence of SEQ ID NO:35, a heavy chain CDR2 region having the amino acid sequence of SEQ ID NO:37, a heavy chain CDR3 region having the amino acid sequence of SEQ ID NO:39, a light chain CDR1 region having the amino acid sequence of SEQ ID NO:43, a light chain CDR2 region having the amino acid sequence of SEQ ID NO:45 and a light chain CDR3 region having the amino acid sequence of SEQ ID NO:47.

14. The diagnostic preparation of claim 6, wherein said monoclonal antibody comprises a heavy chain CDR1 region having the amino acid sequence of SEQ ID NO:51, a heavy chain CDR2 region having the amino acid sequence of SEQ ID NO:53, a heavy chain CDR3 region having the amino acid sequence of SEQ ID NO:55, a light chain CDR1 region having the amino acid sequence of SEQ ID NO:59, a light chain CDR2 region having the amino acid sequence of SEQ ID NO:61 and a light chain CDR3 region having the amino acid sequence of SEQ ID NO:63.

15. A substantially pure monoclonal antibody that binds a conformational epitope of A33 antigen to which the monoclonal antibody of claim 7 binds.

16. A substantially pure monoclonal antibody that binds to a conformational epitope of A33 antigen to which the monoclonal antibody of claim 10 binds.

17. A method for inhibiting Orthopoxvirus infection comprising:

administering to a patient an effective amount of the pharmaceutical preparation of claim 5 to inhibit said Orthopoxvirus infection.

18. A method for a diagnosis of Orthopoxvirus infection comprising:

obtaining the diagnostic preparation of claim 6;

administering to a patient an effective amount of the diagnostic preparation; and detecting binding of the monoclonal antibody as a determination of a presence of Orthopoxvirus.

19. A method of detecting a presence of Orthopoxvirus in a biological sample comprising:

obtaining the diagnostic preparation of claim 6;

contacting said sample with the diagnostic preparation; and assaying binding of the monoclonal antibody as a determination of the presence of said Orthopoxvirus.

* * * * *

SEQUENCE LISTING

<160> NUMBER OF SEQ ID NOS: 88

<210> SEQ ID NO 1
<211> LENGTH: 120
<212> TYPE: PRT
<213> ORGANISM: Pan troglodytes

<400> SEQUENCE: 1

```
Glu Val Gln Leu Leu Glu Ser Gly Gly Gly Leu Ile Lys Pro Gly Gly
 1               5                  10                  15

Ser Leu Arg Leu Ser Cys Ala Ala Ser Gly Phe Ile Phe Arg Asp Tyr
            20                  25                  30

Asn Ile Asn Trp Val Arg Gln Ala Pro Gly Lys Gly Leu Glu Trp Leu
        35                  40                  45

Gly Phe Ile Arg Thr Arg Ala Ser Gly Arg Ser Thr Glu Tyr Ser Ala
    50                  55                  60

Ser Val Lys Gly Arg Phe Thr Ile Ser Arg Asp Asp Ser Lys Asn Ile
```

```
                65                  70                  75                  80
Ala Tyr Leu His Ile Asn Ser Leu Lys Met Glu Asp Thr Ala Val Tyr
                        85                  90                  95
Tyr Cys Ala Lys Lys Gly Asp Ser Tyr Tyr Tyr Met Asp Phe Trp Gly
                100                 105                 110
Lys Gly Thr Ala Val Thr Val Ser
        115                 120

<210> SEQ ID NO 2
<211> LENGTH: 30
<212> TYPE: PRT
<213> ORGANISM: Pan troglodytes

<400> SEQUENCE: 2

Glu Val Gln Leu Leu Glu Ser Gly Gly Gly Leu Ile Lys Pro Gly Gly
1               5                   10                  15

Ser Leu Arg Leu Ser Cys Ala Ala Ser Gly Phe Ile Phe Arg
            20                  25                  30

<210> SEQ ID NO 3
<211> LENGTH: 5
<212> TYPE: PRT
<213> ORGANISM: Pan troglodytes

<400> SEQUENCE: 3

Asp Tyr Asn Ile Asn
1               5

<210> SEQ ID NO 4
<211> LENGTH: 14
<212> TYPE: PRT
<213> ORGANISM: Pan troglodytes

<400> SEQUENCE: 4

Trp Val Arg Gln Ala Pro Gly Lys Gly Leu Glu Trp Leu Gly
1               5                   10

<210> SEQ ID NO 5
<211> LENGTH: 12
<212> TYPE: PRT
<213> ORGANISM: Pan troglodytes

<400> SEQUENCE: 5

Phe Ile Arg Thr Arg Ala Ser Gly Arg Ser Thr Glu
1               5                   10

<210> SEQ ID NO 6
<211> LENGTH: 39
<212> TYPE: PRT
<213> ORGANISM: Pan troglodytes

<400> SEQUENCE: 6

Tyr Ser Ala Ser Val Lys Gly Arg Phe Thr Ile Ser Arg Asp Asp Ser
1               5                   10                  15

Lys Asn Ile Ala Tyr Leu His Ile Asn Ser Leu Lys Met Glu Asp Thr
            20                  25                  30

Ala Val Tyr Tyr Cys Ala Lys
        35

<210> SEQ ID NO 7
<211> LENGTH: 10
<212> TYPE: PRT
<213> ORGANISM: Pan troglodytes
```

<400> SEQUENCE: 7

Lys Gly Asp Ser Tyr Tyr Tyr Met Asp Phe
1               5                   10

<210> SEQ ID NO 8
<211> LENGTH: 10
<212> TYPE: PRT
<213> ORGANISM: Pan troglodytes

<400> SEQUENCE: 8

Trp Gly Lys Gly Thr Ala Val Thr Val Ser
1               5                   10

<210> SEQ ID NO 9
<211> LENGTH: 112
<212> TYPE: PRT
<213> ORGANISM: Pan troglodytes

<400> SEQUENCE: 9

Glu Leu Ala Leu Thr Gln Pro Ala Ser Val Ser Gly Ser Pro Gly Gln
1               5                   10                  15

Ser Ile Thr Ile Ser Cys Thr Gly Gly Arg Ser Asp Leu Gly Asp Ser
            20                  25                  30

Asn Phe Val Ser Trp Tyr Gln Gln Tyr Pro Gly Lys Ala Pro Lys Leu
        35                  40                  45

Leu Ile Tyr Gln Val Asn Lys Arg Pro Ser Gly Val Pro Asp Arg Phe
    50                  55                  60

Ser Ala Ser Lys Ser Ala Asn Thr Ala Ser Leu Thr Ile Ser Gly Leu
65                  70                  75                  80

Gln Thr Glu Asp Glu Ala Asp Tyr Phe Cys Ser Ser Tyr Thr Thr Thr
                85                  90                  95

Ser Thr Tyr Val Phe Gly Ile Gly Thr Lys Val Val Val Leu Gly Gln
            100                 105                 110

<210> SEQ ID NO 10
<211> LENGTH: 22
<212> TYPE: PRT
<213> ORGANISM: Pan troglodytes

<400> SEQUENCE: 10

Glu Leu Ala Leu Thr Gln Pro Ala Ser Val Ser Gly Ser Pro Gly Gln
1               5                   10                  15

Ser Ile Thr Ile Ser Cys
            20

<210> SEQ ID NO 11
<211> LENGTH: 14
<212> TYPE: PRT
<213> ORGANISM: Pan troglodytes

<400> SEQUENCE: 11

Thr Gly Gly Arg Ser Asp Leu Gly Asp Ser Asn Phe Val Ser
1               5                   10

<210> SEQ ID NO 12
<211> LENGTH: 15
<212> TYPE: PRT
<213> ORGANISM: Pan troglodytes

<400> SEQUENCE: 12

Trp Tyr Gln Gln Tyr Pro Gly Lys Ala Pro Lys Leu Leu Ile Tyr
1               5                   10                  15

-continued

```
                1               5                  10                  15
```

<210> SEQ ID NO 13
<211> LENGTH: 7
<212> TYPE: PRT
<213> ORGANISM: Pan troglodytes

<400> SEQUENCE: 13

```
Gln Val Asn Lys Arg Pro Ser
 1               5
```

<210> SEQ ID NO 14
<211> LENGTH: 32
<212> TYPE: PRT
<213> ORGANISM: Pan troglodytes

<400> SEQUENCE: 14

```
Gly Val Pro Asp Arg Phe Ser Ala Ser Lys Ser Ala Asn Thr Ala Ser
 1               5                  10                  15

Leu Thr Ile Ser Gly Leu Gln Thr Glu Asp Glu Ala Asp Tyr Phe Cys
            20                  25                  30
```

<210> SEQ ID NO 15
<211> LENGTH: 10
<212> TYPE: PRT
<213> ORGANISM: Pan troglodytes

<400> SEQUENCE: 15

```
Ser Ser Tyr Thr Thr Thr Ser Thr Tyr Val
 1               5                  10
```

<210> SEQ ID NO 16
<211> LENGTH: 12
<212> TYPE: PRT
<213> ORGANISM: Pan troglodytes

<400> SEQUENCE: 16

```
Phe Gly Ile Gly Thr Lys Val Val Val Leu Gly Gln
 1               5                  10
```

<210> SEQ ID NO 17
<211> LENGTH: 120
<212> TYPE: PRT
<213> ORGANISM: Pan troglodytes

<400> SEQUENCE: 17

```
Glu Val Gln Leu Leu Glu Ser Gly Gly Gly Leu Ile Lys Pro Gly Gly
 1               5                  10                  15

Ser Leu Arg Leu Ser Cys Ala Ala Ser Gly Phe Ile Phe Arg Asp Tyr
            20                  25                  30

Asn Ile Asn Trp Val Arg Gln Ala Pro Gly Lys Gly Leu Glu Trp Leu
        35                  40                  45

Gly Phe Ile Arg Thr Arg Ala Ser Gly Arg Ser Thr Glu Tyr Ser Ala
    50                  55                  60

Ser Val Lys Gly Arg Phe Thr Ile Ser Arg Asp Asp Ser Lys Asn Ile
65                  70                  75                  80

Ala Tyr Leu His Ile Asn Ser Leu Lys Met Glu Asp Thr Ala Val Tyr
                85                  90                  95

Tyr Cys Ala Lys Lys Gly Asp Ser Tyr Tyr Tyr Met Asp Phe Trp Gly
            100                 105                 110

Lys Gly Thr Ala Val Thr Val Ser
        115                 120
```

```
<210> SEQ ID NO 18
<211> LENGTH: 30
<212> TYPE: PRT
<213> ORGANISM: Pan troglodytes

<400> SEQUENCE: 18

Glu Val Gln Leu Leu Glu Ser Gly Gly Gly Leu Ile Lys Pro Gly Gly
 1               5                  10                  15

Ser Leu Arg Leu Ser Cys Ala Ala Ser Gly Phe Ile Phe Arg
            20                  25                  30

<210> SEQ ID NO 19
<211> LENGTH: 5
<212> TYPE: PRT
<213> ORGANISM: Pan troglodytes

<400> SEQUENCE: 19

Asp Tyr Asn Ile Asn
 1               5

<210> SEQ ID NO 20
<211> LENGTH: 14
<212> TYPE: PRT
<213> ORGANISM: Pan troglodytes

<400> SEQUENCE: 20

Trp Val Arg Gln Ala Pro Gly Lys Gly Leu Glu Trp Leu Gly
 1               5                  10

<210> SEQ ID NO 21
<211> LENGTH: 12
<212> TYPE: PRT
<213> ORGANISM: Pan troglodytes

<400> SEQUENCE: 21

Phe Ile Arg Thr Arg Ala Ser Gly Arg Ser Thr Glu
 1               5                  10

<210> SEQ ID NO 22
<211> LENGTH: 39
<212> TYPE: PRT
<213> ORGANISM: Pan troglodytes

<400> SEQUENCE: 22

Tyr Ser Ala Ser Val Lys Gly Arg Phe Thr Ile Ser Arg Asp Asp Ser
 1               5                  10                  15

Lys Asn Ile Ala Tyr Leu His Ile Asn Ser Leu Lys Met Glu Asp Thr
            20                  25                  30

Ala Val Tyr Tyr Cys Ala Lys
        35

<210> SEQ ID NO 23
<211> LENGTH: 10
<212> TYPE: PRT
<213> ORGANISM: Pan troglodytes

<400> SEQUENCE: 23

Lys Gly Asp Ser Tyr Tyr Tyr Met Asp Phe
 1               5                  10

<210> SEQ ID NO 24
<211> LENGTH: 10
<212> TYPE: PRT
```

<213> ORGANISM: Pan troglodytes

<400> SEQUENCE: 24

Trp Gly Lys Gly Thr Ala Val Thr Val Ser
1               5                   10

<210> SEQ ID NO 25
<211> LENGTH: 112
<212> TYPE: PRT
<213> ORGANISM: Pan troglodytes

<400> SEQUENCE: 25

Glu Leu Ala Leu Thr Gln Pro Pro Ser Val Ser Gly Ser Pro Gly Gln
1               5                   10                  15

Ser Ile Thr Ile Ser Cys Thr Gly Thr Ser Ser Asp Val Gly Gly His
            20                  25                  30

Asn Gly Val Ser Trp Tyr Gln Gln Tyr Pro Gly Lys Ala Pro Lys Val
        35                  40                  45

Met Ile Tyr Glu Val Asn Lys Arg Pro Ser Gly Val Ser Asn Arg Leu
    50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Ser Ser Tyr Arg Asn Gly
                85                  90                  95

Gly Ser Val Val Phe Gly Gly Gly Thr Lys Leu Thr Val Leu Gly Gln
            100                 105                 110

<210> SEQ ID NO 26
<211> LENGTH: 22
<212> TYPE: PRT
<213> ORGANISM: Pan troglodytes

<400> SEQUENCE: 26

Glu Leu Ala Leu Thr Gln Pro Pro Ser Val Ser Gly Ser Pro Gly Gln
1               5                   10                  15

Ser Ile Thr Ile Ser Cys
            20

<210> SEQ ID NO 27
<211> LENGTH: 14
<212> TYPE: PRT
<213> ORGANISM: Pan troglodytes

<400> SEQUENCE: 27

Thr Gly Thr Ser Ser Asp Val Gly Gly His Asn Gly Val Ser
1               5                   10

<210> SEQ ID NO 28
<211> LENGTH: 15
<212> TYPE: PRT
<213> ORGANISM: Pan troglodytes

<400> SEQUENCE: 28

Trp Tyr Gln Gln Tyr Pro Gly Lys Ala Pro Lys Val Met Ile Tyr
1               5                   10                  15

<210> SEQ ID NO 29
<211> LENGTH: 7
<212> TYPE: PRT
<213> ORGANISM: Pan troglodytes

<400> SEQUENCE: 29

```
Glu Val Asn Lys Arg Pro Ser
  1               5
```

<210> SEQ ID NO 30
<211> LENGTH: 32
<212> TYPE: PRT
<213> ORGANISM: Pan troglodytes

<400> SEQUENCE: 30

```
Gly Val Ser Asn Arg Leu Ser Gly Ser Lys Ser Gly Asn Thr Ala Ser
  1               5                  10                  15

Leu Thr Ile Ser Gly Leu Gln Ala Glu Asp Glu Gly Asp Tyr Tyr Cys
                 20                  25                  30
```

<210> SEQ ID NO 31
<211> LENGTH: 10
<212> TYPE: PRT
<213> ORGANISM: Pan troglodytes

<400> SEQUENCE: 31

```
Ser Ser Tyr Arg Asn Gly Gly Ser Val Val
  1               5                  10
```

<210> SEQ ID NO 32
<211> LENGTH: 12
<212> TYPE: PRT
<213> ORGANISM: Pan troglodytes

<400> SEQUENCE: 32

```
Phe Gly Gly Gly Thr Lys Leu Thr Val Leu Gly Gln
  1               5                  10
```

<210> SEQ ID NO 33
<211> LENGTH: 123
<212> TYPE: PRT
<213> ORGANISM: Pan troglodytes

<400> SEQUENCE: 33

```
Glu Val Gln Leu Glu Gln Ser Gly Ser Glu Val Lys Lys Pro Gly Ala
  1               5                  10                  15

Ser Val Lys Leu Ser Cys Lys Ala Ser Gly Tyr Thr Phe Thr Ser Tyr
                 20                  25                  30

Ser Leu Gly Trp Val Arg Gln Ala Pro Gly Gln Gly Leu Glu Trp Met
             35                  40                  45

Gly Trp Ile Asn Thr Lys Thr Gly Asn Pro Thr Tyr Ala Gln Gly Phe
         50                  55                  60

Thr Gly Arg Phe Val Phe Ser Leu Asp Thr Ser Val Asn Thr Ala Tyr
 65                  70                  75                  80

Leu Gln Ile Thr Ser Leu Lys Ala Glu Asp Thr Ala Val Tyr Phe Cys
                 85                  90                  95

Ala Lys Gly Thr Phe Tyr Tyr Gly Trp Gly Pro Tyr Tyr Asn Trp Phe
                100                 105                 110

Asp Pro Trp Gly Gln Gly Ala Leu Val Thr Val
            115                 120
```

<210> SEQ ID NO 34
<211> LENGTH: 30
<212> TYPE: PRT
<213> ORGANISM: Pan troglodytes

<400> SEQUENCE: 34

```
Glu Val Gln Leu Glu Gln Ser Gly Ser Glu Val Lys Lys Pro Gly Ala
  1               5                  10                  15
```

```
                1               5                  10                  15
Ser Val Lys Leu Ser Cys Lys Ala Ser Gly Tyr Thr Phe Thr
                20                  25                  30

<210> SEQ ID NO 35
<211> LENGTH: 5
<212> TYPE: PRT
<213> ORGANISM: Pan troglodytes

<400> SEQUENCE: 35

Ser Tyr Ser Leu Gly
1               5

<210> SEQ ID NO 36
<211> LENGTH: 14
<212> TYPE: PRT
<213> ORGANISM: Pan troglodytes

<400> SEQUENCE: 36

Trp Val Arg Gln Ala Pro Gly Gln Gly Leu Glu Trp Met Gly
1               5                  10

<210> SEQ ID NO 37
<211> LENGTH: 10
<212> TYPE: PRT
<213> ORGANISM: Pan troglodytes

<400> SEQUENCE: 37

Trp Ile Asn Thr Lys Thr Gly Asn Pro Thr
1               5                  10

<210> SEQ ID NO 38
<211> LENGTH: 39
<212> TYPE: PRT
<213> ORGANISM: Pan troglodytes

<400> SEQUENCE: 38

Tyr Ala Gln Gly Phe Thr Gly Arg Phe Val Phe Ser Leu Asp Thr Ser
1               5                  10                  15

Val Asn Thr Ala Tyr Leu Gln Ile Thr Ser Leu Lys Ala Glu Asp Thr
                20                  25                  30

Ala Val Tyr Phe Cys Ala Lys
        35

<210> SEQ ID NO 39
<211> LENGTH: 16
<212> TYPE: PRT
<213> ORGANISM: Pan troglodytes

<400> SEQUENCE: 39

Gly Thr Phe Tyr Tyr Gly Trp Gly Pro Tyr Tyr Asn Trp Phe Asp Pro
1               5                  10                  15

<210> SEQ ID NO 40
<211> LENGTH: 9
<212> TYPE: PRT
<213> ORGANISM: Pan troglodytes

<400> SEQUENCE: 40

Trp Gly Gln Gly Ala Leu Val Thr Val
1               5

<210> SEQ ID NO 41
<211> LENGTH: 113
```

<212> TYPE: PRT
<213> ORGANISM: Pan troglodytes

<400> SEQUENCE: 41

Ala Glu Leu Val Leu Thr Gln Pro Pro Ser Val Ser Ala Ala Pro Gly
1               5                   10                  15

Gln Lys Ile Thr Ile Ser Cys Ser Gly Ser Gly Ser Asn Ile Gly Arg
            20                  25                  30

His Tyr Val Ser Trp Tyr Gln Gln Phe Pro Gly Thr Ala Pro Lys Ile
        35                  40                  45

Leu Ile Tyr Asp Asn Asp Lys Arg Pro Ser Gly Ile Ser Asp Arg Phe
    50                  55                  60

Ser Gly Ser Lys Ser Gly Ala Ser Ala Thr Leu Asp Ile Thr Gly Leu
65                  70                  75                  80

Gln Thr Gly Asp Glu Ala Asp Tyr Tyr Cys Ala Thr Trp Asp Thr Asn
                85                  90                  95

Leu Ser Gly Gly Val Phe Gly Gly Thr Lys Val Thr Val Leu Gly
            100                 105                 110

Gln

<210> SEQ ID NO 42
<211> LENGTH: 23
<212> TYPE: PRT
<213> ORGANISM: Pan troglodytes

<400> SEQUENCE: 42

Ala Glu Leu Val Leu Thr Gln Pro Pro Ser Val Ser Ala Ala Pro Gly
1               5                   10                  15

Gln Lys Ile Thr Ile Ser Cys
            20

<210> SEQ ID NO 43
<211> LENGTH: 13
<212> TYPE: PRT
<213> ORGANISM: Pan troglodytes

<400> SEQUENCE: 43

Ser Gly Ser Gly Ser Asn Ile Gly Arg His Tyr Val Ser
1               5                   10

<210> SEQ ID NO 44
<211> LENGTH: 15
<212> TYPE: PRT
<213> ORGANISM: Pan troglodytes

<400> SEQUENCE: 44

Trp Tyr Gln Gln Phe Pro Gly Thr Ala Pro Lys Ile Leu Ile Tyr
1               5                   10                  15

<210> SEQ ID NO 45
<211> LENGTH: 7
<212> TYPE: PRT
<213> ORGANISM: Pan troglodytes

<400> SEQUENCE: 45

Asp Asn Asp Lys Arg Pro Ser
1               5

<210> SEQ ID NO 46
<211> LENGTH: 32
<212> TYPE: PRT
<213> ORGANISM: Pan troglodytes

```
<400> SEQUENCE: 46

Gly Ile Ser Asp Arg Phe Ser Gly Ser Lys Ser Gly Ala Ser Ala Thr
1               5                   10                  15

Leu Asp Ile Thr Gly Leu Gln Thr Gly Asp Glu Ala Asp Tyr Tyr Cys
            20                  25                  30

<210> SEQ ID NO 47
<211> LENGTH: 11
<212> TYPE: PRT
<213> ORGANISM: Pan troglodytes

<400> SEQUENCE: 47

Ala Thr Trp Asp Thr Asn Leu Ser Gly Gly Val
1               5                   10

<210> SEQ ID NO 48
<211> LENGTH: 12
<212> TYPE: PRT
<213> ORGANISM: Pan troglodytes

<400> SEQUENCE: 48

Phe Gly Gly Gly Thr Lys Val Thr Val Leu Gly Gln
1               5                   10

<210> SEQ ID NO 49
<211> LENGTH: 126
<212> TYPE: PRT
<213> ORGANISM: Pan troglodytes

<400> SEQUENCE: 49

Glu Val Gln Leu Glu Ser Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Thr Ile His Trp Val Arg Gln Ala Pro Gly Gln Arg Leu Glu Trp Met
        35                  40                  45

Gly Trp Ile Asn Thr Ala Val Gly Asn Thr Lys Phe Ser Gln Ser Leu
    50                  55                  60

Gln Gly Arg Val Thr Ile Thr Arg Asp Thr Ser Ala Asn Thr Ala Tyr
65                  70                  75                  80

Met Glu Leu Ser Ser Leu Arg Ser Glu Asp Thr Ala Ile Tyr Tyr Cys
                85                  90                  95

Ala Arg Asp Pro Ile Leu Tyr Tyr Gly Trp Gly Ser Tyr Arg Val Ala
            100                 105                 110

Gly Tyr Phe Asp Tyr Trp Gly Gln Gly Ser Leu Val Thr Val
        115                 120                 125

<210> SEQ ID NO 50
<211> LENGTH: 30
<212> TYPE: PRT
<213> ORGANISM: Pan troglodytes

<400> SEQUENCE: 50

Glu Val Gln Leu Glu Ser Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 51
<211> LENGTH: 5
```

```
<212> TYPE: PRT
<213> ORGANISM: Pan troglodytes

<400> SEQUENCE: 51

Lys Tyr Thr Ile His
1               5

<210> SEQ ID NO 52
<211> LENGTH: 14
<212> TYPE: PRT
<213> ORGANISM: Pan troglodytes

<400> SEQUENCE: 52

Trp Val Arg Gln Ala Pro Gly Gln Arg Leu Glu Trp Met Gly
1               5                   10

<210> SEQ ID NO 53
<211> LENGTH: 10
<212> TYPE: PRT
<213> ORGANISM: Pan troglodytes

<400> SEQUENCE: 53

Trp Ile Asn Thr Ala Val Gly Asn Thr Lys
1               5                   10

<210> SEQ ID NO 54
<211> LENGTH: 39
<212> TYPE: PRT
<213> ORGANISM: Pan troglodytes

<400> SEQUENCE: 54

Phe Ser Gln Ser Leu Gln Gly Arg Val Thr Ile Thr Arg Asp Thr Ser
1               5                   10                  15

Ala Asn Thr Ala Tyr Met Glu Leu Ser Ser Leu Arg Ser Glu Asp Thr
            20                  25                  30

Ala Ile Tyr Tyr Cys Ala Arg
        35

<210> SEQ ID NO 55
<211> LENGTH: 19
<212> TYPE: PRT
<213> ORGANISM: Pan troglodytes

<400> SEQUENCE: 55

Asp Pro Ile Leu Tyr Tyr Gly Trp Gly Ser Tyr Arg Val Ala Gly Tyr
1               5                   10                  15

Phe Asp Tyr

<210> SEQ ID NO 56
<211> LENGTH: 9
<212> TYPE: PRT
<213> ORGANISM: Pan troglodytes

<400> SEQUENCE: 56

Trp Gly Gln Gly Ser Leu Val Thr Val
1               5

<210> SEQ ID NO 57
<211> LENGTH: 110
<212> TYPE: PRT
<213> ORGANISM: Pan troglodytes

<400> SEQUENCE: 57

Ala Glu Leu Val Leu Thr Gln Pro Pro Ser Val Ser Val Tyr Pro Gly
```

```
                1               5                   10                  15
Gln Thr Ala Ser Ile Thr Cys Ser Gly Asp Lys Leu Gly Asp Lys Tyr
                20                  25                  30

Val Ser Trp Tyr Gln Gln Lys Ser Ala Gln Pro Pro Val Leu Val Ile
            35                  40                  45

His Gly Asp Asn Lys Arg Pro Ser Gly Ile Pro Glu Arg Phe Ser Gly
        50                  55                  60

Ser Asn Ser Gly Asn Thr Ala Thr Leu Thr Ile Ser Gly Thr Gln Ala
65                  70                  75                  80

Ile Asp Glu Ala Asp Tyr Tyr Cys Gln Thr Trp Asp Ser Tyr Thr Phe
                85                  90                  95

Leu Leu Phe Gly Gly Gly Thr Lys Leu Thr Ala Leu Ser Gln
            100                 105                 110

<210> SEQ ID NO 58
<211> LENGTH: 23
<212> TYPE: PRT
<213> ORGANISM: Pan troglodytes

<400> SEQUENCE: 58

Ala Glu Leu Val Leu Thr Gln Pro Pro Ser Val Ser Val Tyr Pro Gly
1               5                   10                  15

Gln Thr Ala Ser Ile Thr Cys
            20

<210> SEQ ID NO 59
<211> LENGTH: 11
<212> TYPE: PRT
<213> ORGANISM: Pan troglodytes

<400> SEQUENCE: 59

Ser Gly Asp Lys Leu Gly Asp Lys Tyr Val Ser
1               5                   10

<210> SEQ ID NO 60
<211> LENGTH: 15
<212> TYPE: PRT
<213> ORGANISM: Pan troglodytes

<400> SEQUENCE: 60

Trp Tyr Gln Gln Lys Ser Ala Gln Pro Pro Val Leu Val Ile His
1               5                   10                  15

<210> SEQ ID NO 61
<211> LENGTH: 7
<212> TYPE: PRT
<213> ORGANISM: Pan troglodytes

<400> SEQUENCE: 61

Gly Asp Asn Lys Arg Pro Ser
1               5

<210> SEQ ID NO 62
<211> LENGTH: 32
<212> TYPE: PRT
<213> ORGANISM: Pan troglodyte

<400> SEQUENCE: 62

Gly Ile Pro Glu Arg Phe Ser Gly Ser Asn Ser Gly Asn Thr Ala Thr
1               5                   10                  15

Leu Thr Ile Ser Gly Thr Gln Ala Ile Asp Glu Ala Asp Tyr Tyr Cys
            20                  25                  30
```

```
<210> SEQ ID NO 63
<211> LENGTH: 10
<212> TYPE: PRT
<213> ORGANISM: Pan troglodyte

<400> SEQUENCE: 63

Gln Thr Trp Asp Ser Tyr Thr Phe Leu Leu
1               5                   10

<210> SEQ ID NO 64
<211> LENGTH: 12
<212> TYPE: PRT
<213> ORGANISM: Pan troglodyte

<400> SEQUENCE: 64

Phe Gly Gly Gly Thr Lys Leu Thr Ala Leu Ser Gln
1               5                   10

<210> SEQ ID NO 65
<211> LENGTH: 125
<212> TYPE: PRT
<213> ORGANISM: Pan troglodyte

<400> SEQUENCE: 65

Glu Val Gln Leu Glu Ser Ser Gly Ala Glu Val Lys Lys Pro Gly Glu
1               5                   10                  15

Ser Leu Lys Ile Ser Cys Lys Gly Ser Gly Tyr Thr Phe Ala Ser Tyr
            20                  25                  30

Trp Ile Val Trp Val Arg Gln Met Pro Gly Lys Gly Leu Glu Tyr Met
        35                  40                  45

Gly Ser Ile Tyr Pro Gly Asp Ser Gly Thr Arg Tyr Ser Pro Ser Phe
    50                  55                  60

Arg Gly Gln Val Thr Ile Ser Ala Asp Lys Ser Ile Asn Thr Ala Tyr
65                  70                  75                  80

Leu Gln Trp Gly Ser Leu Lys Ala Ser Asp Thr Ala Phe Tyr Tyr Cys
                85                  90                  95

Ala Arg Leu Lys Pro Leu Arg Gly Ser Leu Phe Gly Glu Pro Ile Gly
            100                 105                 110

Pro Tyr Asp Tyr Trp Gly Gln Ala Thr Leu Val Thr Val
        115                 120                 125

<210> SEQ ID NO 66
<211> LENGTH: 30
<212> TYPE: PRT
<213> ORGANISM: Pan troglodyte

<400> SEQUENCE: 66

Glu Val Gln Leu Glu Ser Ser Gly Ala Glu Val Lys Lys Pro Gly Glu
1               5                   10                  15

Ser Leu Lys Ile Ser Cys Lys Gly Ser Gly Tyr Thr Phe Ala
            20                  25                  30

<210> SEQ ID NO 67
<211> LENGTH: 5
<212> TYPE: PRT
<213> ORGANISM: Pan troglodytes

<400> SEQUENCE: 67

Ser Tyr Trp Ile Val
1               5
```

```
<210> SEQ ID NO 68
<211> LENGTH: 14
<212> TYPE: PRT
<213> ORGANISM: Pan troglodytes

<400> SEQUENCE: 68

Trp Val Arg Gln Met Pro Gly Lys Gly Leu Glu Tyr Met Gly
1               5                   10

<210> SEQ ID NO 69
<211> LENGTH: 10
<212> TYPE: PRT
<213> ORGANISM: Pan troglodytes

<400> SEQUENCE: 69

Ser Ile Tyr Pro Gly Asp Ser Gly Thr Arg
1               5                   10

<210> SEQ ID NO 70
<211> LENGTH: 39
<212> TYPE: PRT
<213> ORGANISM: Pan troglodytes

<400> SEQUENCE: 70

Tyr Ser Pro Ser Phe Arg Gly Gln Val Thr Ile Ser Ala Asp Lys Ser
1               5                   10                  15

Ile Asn Thr Ala Tyr Leu Gln Trp Gly Ser Leu Lys Ala Ser Asp Thr
            20                  25                  30

Ala Phe Tyr Tyr Cys Ala Arg
        35

<210> SEQ ID NO 71
<211> LENGTH: 18
<212> TYPE: PRT
<213> ORGANISM: Pan troglodytes

<400> SEQUENCE: 71

Leu Lys Pro Leu Arg Gly Ser Leu Phe Gly Glu Pro Ile Gly Pro Tyr
1               5                   10                  15

Asp Tyr

<210> SEQ ID NO 72
<211> LENGTH: 9
<212> TYPE: PRT
<213> ORGANISM: Pan troglodytes

<400> SEQUENCE: 72

Trp Gly Gln Ala Thr Leu Val Thr Val
1               5

<210> SEQ ID NO 73
<211> LENGTH: 113
<212> TYPE: PRT
<213> ORGANISM: Pan troglodytes

<400> SEQUENCE: 73

Ala Glu Leu Ala Leu Thr Gln Pro Ala Ser Val Ser Gly Ser Pro Gly
1               5                   10                  15

Gln Ser Ile Thr Ile Ser Cys Thr Gly Thr Ser Ser Asp Val Gly Gly
            20                  25                  30

Tyr Asn Ala Val Ser Trp Tyr Gln Gln His Pro Gly Lys Ala Pro Lys
        35                  40                  45
```

-continued

```
Leu Met Ile Tyr Glu Val Asn Lys Arg Pro Ser Gly Val Ser Asn Arg
 50                  55                  60
Phe Ser Gly Ser Lys Ser Gly Asn Thr Ala Ser Leu Thr Ile Ser Gly
 65                  70                  75                  80
Leu Gln Ala Glu Asp Glu Ala Asp Tyr Tyr Cys Ser Ser Tyr Arg Ser
                 85                  90                  95
Gly Gly Thr Val Val Phe Gly Gly Gly Thr Lys Leu Thr Val Leu Gly
            100                 105                 110
Gln

<210> SEQ ID NO 74
<211> LENGTH: 23
<212> TYPE: PRT
<213> ORGANISM: Pan troglodytes

<400> SEQUENCE: 74

Ala Glu Leu Ala Leu Thr Gln Pro Ala Ser Val Ser Gly Ser Pro Gly
 1               5                  10                  15
Gln Ser Ile Thr Ile Ser Cys
             20

<210> SEQ ID NO 75
<211> LENGTH: 14
<212> TYPE: PRT
<213> ORGANISM: Pan troglodytes

<400> SEQUENCE: 75

Thr Gly Thr Ser Ser Asp Val Gly Gly Tyr Asn Ala Val Ser
 1               5                  10

<210> SEQ ID NO 76
<211> LENGTH: 15
<212> TYPE: PRT
<213> ORGANISM: Pan troglodytes

<400> SEQUENCE: 76

Trp Tyr Gln Gln His Pro Gly Lys Ala Pro Lys Leu Met Ile Tyr
 1               5                  10                  15

<210> SEQ ID NO 77
<211> LENGTH: 7
<212> TYPE: PRT
<213> ORGANISM: Pan troglodytes

<400> SEQUENCE: 77

Glu Val Asn Lys Arg Pro Ser
 1               5

<210> SEQ ID NO 78
<211> LENGTH: 32
<212> TYPE: PRT
<213> ORGANISM: Pan troglodytes

<400> SEQUENCE: 78

Gly Val Ser Asn Arg Phe Ser Gly Ser Lys Ser Gly Asn Thr Ala Ser
 1               5                  10                  15
Leu Thr Ile Ser Gly Leu Gln Ala Glu Asp Glu Ala Asp Tyr Tyr Cys
             20                  25                  30

<210> SEQ ID NO 79
<211> LENGTH: 10
<212> TYPE: PRT
<213> ORGANISM: Pan troglodytes
```

<400> SEQUENCE: 79

Ser Ser Tyr Arg Ser Gly Gly Thr Val Val
1               5                   10

<210> SEQ ID NO 80
<211> LENGTH: 12
<212> TYPE: PRT
<213> ORGANISM: Pan troglodytes

<400> SEQUENCE: 80

Phe Gly Gly Gly Thr Lys Leu Thr Val Leu Gly Gln
1               5                   10

<210> SEQ ID NO 81
<211> LENGTH: 29
<212> TYPE: DNA
<213> ORGANISM: Artificial Sequence
<220> FEATURE:
<223> OTHER INFORMATION: synthetic primer

<400> SEQUENCE: 81
aactgcagac atgtactgta cccactatg                                    29

<210> SEQ ID NO 82
<211> LENGTH: 27
<212> TYPE: DNA
<213> ORGANISM: Artificial Sequence
<220> FEATURE:
<223> OTHER INFORMATION: synthetic primer

<400> SEQUENCE: 82
tgattcggga tattattctt tggatcc                                      27

<210> SEQ ID NO 83
<211> LENGTH: 27
<212> TYPE: DNA
<213> ORGANISM: Artificial Sequence
<220> FEATURE:
<223> OTHER INFORMATION: synthetic primer

<400> SEQUENCE: 83
ggatccaaag aataatatcc cgaatca                                      27

<210> SEQ ID NO 84
<211> LENGTH: 24
<212> TYPE: DNA
<213> ORGANISM: Artificial Sequence
<220> FEATURE:
<223> OTHER INFORMATION: synthetic primer

<400> SEQUENCE: 84
acagtttctg attacgtctc tgaa                                         24

<210> SEQ ID NO 85
<211> LENGTH: 24
<212> TYPE: DNA
<213> ORGANISM: Artificial Sequence
<220> FEATURE:
<223> OTHER INFORMATION: synthetic primer

<400> SEQUENCE: 85
ttcagagacg taatcagaaa ctgt                                         24

<210> SEQ ID NO 86
<211> LENGTH: 33

-continued

```
<212> TYPE: DNA
<213> ORGANISM: Artificial Sequence
<220> FEATURE:
<223> OTHER INFORMATION: synthetic primer

<400> SEQUENCE: 86
aatgccatca tcacactaat ttgcaaggac gaa                                33

<210> SEQ ID NO 87
<211> LENGTH: 33
<212> TYPE: DNA
<213> ORGANISM: Artificial Sequence
<220> FEATURE:
<223> OTHER INFORMATION: synthetic primer

<400> SEQUENCE: 87
ttcgtccttg caaattagtg tgatgatggc att                                33

<210> SEQ ID NO 88
<211> LENGTH: 29
<212> TYPE: DNA
<213> ORGANISM: Artificial Sequence
<220> FEATURE:
<223> OTHER INFORMATION: synthetic primer

<400> SEQUENCE: 88
aaaagcttac attccgcatt aggacacgt                                     29
```